(12) United States Patent
Mudde et al.

(10) Patent No.: US 10,328,134 B2
(45) Date of Patent: Jun. 25, 2019

(54) GASTRIN PEPTIDE IMMUNOGENIC COMPOSITION

(71) Applicant: TYG ONCOLOGY LTD., Nottinghamshire (GB)

(72) Inventors: Geert Cornelius Mudde, Breitenfurt (AT); Paul Christopher Broome, Luton (GB); Frederick William Jacobs, Derbyshire (GB); Christof Langer, Vienna (AT)

(73) Assignee: TYG ONCOLOGY LTD., Nottinghamshire (GB)

(*) Notice: Subject to any disclaimer, the term of this patent is extended or adjusted under 35 U.S.C. 154(b) by 0 days.

(21) Appl. No.: 14/892,973

(22) PCT Filed: May 16, 2014

(86) PCT No.: PCT/EP2014/060088
§ 371 (c)(1),
(2) Date: Nov. 20, 2015

(87) PCT Pub. No.: WO2014/187743
PCT Pub. Date: Nov. 27, 2014

(65) Prior Publication Data
US 2016/0129096 A1 May 12, 2016

(30) Foreign Application Priority Data
May 21, 2013 (EP) ...................................... 13168565

(51) Int. Cl.
| | | |
|---|---|---|
| *A61K 39/00* | (2006.01) | |
| *A61K 39/39* | (2006.01) | |
| *A61K 45/06* | (2006.01) | |
| *C07K 16/28* | (2006.01) | |
| *A61K 47/54* | (2017.01) | |
| *A61K 47/68* | (2017.01) | |

(52) U.S. Cl.
CPC ...... *A61K 39/0011* (2013.01); *A61K 39/0005* (2013.01); *A61K 39/39* (2013.01); *A61K 45/06* (2013.01); *A61K 47/549* (2017.08); *A61K 47/6849* (2017.08); *C07K 16/283* (2013.01); A61K 2039/505 (2013.01); A61K 2039/55516 (2013.01); A61K 2039/55561 (2013.01); A61K 2039/585 (2013.01); A61K 2039/6031 (2013.01); A61K 2039/627 (2013.01); C07K 2317/524 (2013.01); C07K 2317/526 (2013.01); C07K 2317/56 (2013.01); C07K 2317/622 (2013.01)

(58) Field of Classification Search
CPC .... A61K 2039/505; A61K 2039/55516; A61K 2039/55561; A61K 2039/585; A61K 2039/6031; A61K 2039/627; A61K 39/0005; A61K 39/0011; A61K 39/39; A61K 45/06; A61K 47/549; A61K 47/6849; C07K 16/283; C07K 2317/524; C07K 2317/526; C07K 2317/56; C07K 2317/622

See application file for complete search history.

(56) References Cited

U.S. PATENT DOCUMENTS

| | | |
|---|---|---|
| 5,023,077 A | 6/1991 | Gevas et al. |
| 5,609,870 A | 3/1997 | Gevas et al. |

FOREIGN PATENT DOCUMENTS

| | | |
|---|---|---|
| EP | 3297547 A1 | 12/2011 |
| JP | H09-505056 | 5/1997 |
| JP | 2009-528071 | 8/2009 |
| RU | 2467747 | 8/2010 |
| WO | WO 97/07218 | 2/1997 |
| WO | 2005095459 | 10/2005 |
| WO | WO 2007/098934 A1 | 9/2007 |
| WO | WO 97/28821 A1 | 12/2011 |
| WO | WO 2014/009209 | 1/2014 |

OTHER PUBLICATIONS

GAST gastrin [*Homo sapiens* (human)]—Gene—NCBI, 2018, pp. 1-7.*

Abel, K., et al., "Deoxycytidyl-Deoxyguanosine Oligonucleotide Classes A, B, and C Induce Distinct Cytokine Gene Expression Patterns in Rhesus Monkey Peripheral Blood Mononuclear Cells and Distinct Alpha Interferon Responses in TLR9-Expressing Rhesus Monkey Plasmacytoid Dendritic Cells," *Clin. Diagn. Lab Immunol.* 12(5):606-621 (2005).

(Continued)

*Primary Examiner* — Thomas S Heard
(74) *Attorney, Agent, or Firm* — Loza & Loza, LLP; Michael F. Fedrick

(57) ABSTRACT

The invention provides for an immunogenic composition comprising a. a directed adjuvant comprising at least an anti-CD32 moiety linked to a TLR9 ligand and a first peptidic alpha-helix; and b. a gastrin-17 peptide immunogen linked to a second peptidic alpha-helix coiled to the first alpha-helix, which peptide immunogen is any of (i) human gastrin-17 comprising the amino acid sequence of SEQ ID 1, or a fragment thereof comprising the amino acid sequence of SEQ ID 2, or at least the 4 N-terminal amino acids of SEQ ID 2; (ii) an analog of (i), preferably of rhesus monkey or murine origin; and/or (iii) a functionally active variant of any of (i) or (ii), with one, two, three or four point mutations in the amino acid sequence of SEQ ID 2. The invention further provides a kit for producing such immunogenic composition, a vaccine comprising such immunogenic composition and its medical use, such as for treating gastrin dependent diseases.

Figure 1:
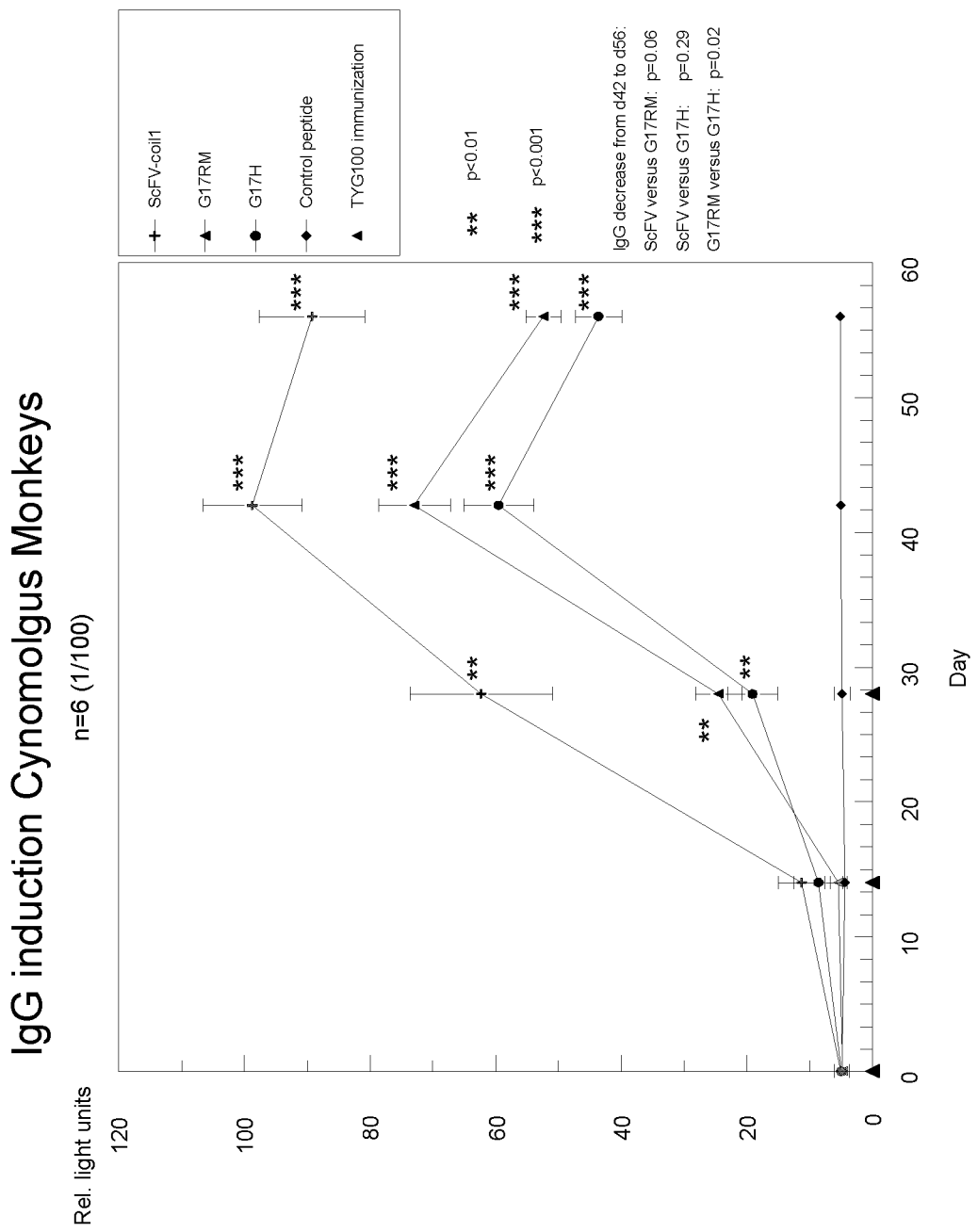

19 Claims, 5 Drawing Sheets
Specification includes a Sequence Listing.

(56) References Cited

OTHER PUBLICATIONS

Arndt, K.M., et al., "Helix-stabilized Fv (hsFv) Antibody Fragments: Substituting the Constant Domains of a Fab Fragment for a Heterodimeric Coiled-coil Domain," *J. Mol. Biol.*: 312, 221-228.

Berntzen, G., et al., "Identification of a High Affinity Fcγ RIIA-binding Peptide that Distinguishes Fcγ RIIA from Fcγ RIIB and Exploits Fcγ RIIA-mediated Phagocytosis and Degradation," *J. Biol. Chem.* 284(2):1126-1135 (2009).

Brett, B.T., et al., "Phase II Study of Anti-Gastrin-17 Antibodies, Raised to G17DT, in Advanced Pancreatic Cancer," *J. Clin. Oncol.* 20(20):4225-4231(2002)

Chao, H., et al., "Use of a heterodintetic coiled-coil system for hiosensor application and affinity purification," *J. Chromatogr. B* 715:307-329 (1998).

Cheever, M.A. and Higano, C.S., "Provenge (Sipuleucel-T) in Prostate Cancer: The First FDA-Approved Therapeutic Cancer Vaccine," *Clin. Cancer Res.* 17:3520-3526 (2011).

Ciccotosto, G.D., et al., "Gastrin Processing and Secretion in Patients with End-Stage Renal Failure," *J. Clin. Endocrinol. Metab.* 81(9):3231-3239 (1996).

Eaton-Bassiri, A., et al., "Toll-like Receptor 9 Can Be Expressed at the Cell Surface of Distinct Populations of Tonsils and Human Peripheral Blood Mononuclear Cells," *Infect. Immun.* 72(12):7202-7211(2004).

Greenman, J., et al., "Characterization of a new monoclonal anti-Fc γ RII antibody, AT10, and its incorporation into a bispecific F(ab')$_2$ derivative for recruitment of cytotoxic effectors," *Mol. Immunol.* 28(11):1243-1254 (1991).

Hartmann, G., et al., "Rational design of new CpG oligonucleotides that combine B cell activation with high IFN-α induction in plasmacytoid dendritic cells," *Eur. J. Immunol.* 33:1633-1641(2003).

Krieg, A.M., et al., "CpG motifs in bacterial DNA trigger direct B-cell activation," *Nature* 374:546-549 (1995).

Krug, A., et al., "Identification of CpG oligonucleotide sequences with high induction of IFN-α/β plasmacytoid dendritic cells," *Eur. J. Immunol.* 31:2154-2163.

Linley, A.J., et al., "Tumour-associated antigens: considerations for their use in tumour immunotherapy," *Int. J. Hematol.* 93:263-273 (2011).

Litowski, J.R. and Hodges, R.S., "Designing Heterodimeric Two-stranded α-Helical Coiled-coils: the effect of chain length on protein folding, stability and specificity," *J. Pept. Res.* 58:477-492 (2001).

Litowski, J.R. and Hodges, R.S., "Designing Heterodimeric Two-stranded α-Helical Coiled-Coils: Effects of hydrophobicity and α-helical propensity on protein folding, stability, and specificity," *J. Biol. Chem.* 277(40):37272-37279 (2002).

Macintyre, E.A., et al., "Mechanism of human monocyte activation via the 40-kDa Fc receptor for IgG," *J Immunol.* 141(12):4333-4343 (1988).

Mathis, D. and Benoist, C., "Back to central tolerance," *Immunity* 20:509-516 (2004).

Miller, J.F.A.P. and Morahan, G., "Peripheral T Cell Tolerance," *Annu. Rev. Immunol.* 10:51-69 (1992).

Morton, M., et al., "Targeting gastrin for the treatment of gastric acid related disorders and pancreatic cancer," *Trends in Pharmacological Sciences* 32(4):201-205 (2011).

Puig, M., et al., "TLR9 and TLR7 agonists mediate distinct type I IFN responses in humans and nonhuman primates in vitro and in vivo," *J Leukoc. Biol.* 91:147-158 (2012).

Rengifo-Cam, W. and Singh, P., "Role of progastrins and gastrins and their receptors in GI and pancreatic cancers: Targets for Treatment," *Curr. Pharm. Des* 10:2345-2358 (2004).

Saikh, K.U., et al., "Human monocytes infected with *Yersinia pestis* express cell surface TLR9 and differentiate into dendritic cells," *J. Immunol.* 173:7426-7434 (2004).

Stuart, S.G., et al., "Isolation and expression of cDNA clones encoding a human receptor for IgG (FcγRII)," *J. Exp. Med.* 166:1668-1684 (1987).

Stuart, S.G., et al., "Human IgG Fc receptor (hFcRII; CD32) exists as multiple isoforms in macrophages, lymphocytes and IgG-transporting placental epithelium," *EMBO J.* 8(12):3657-3666 (1989).

Tafuri, A., et al., "T cell awareness of paternal alloantigens during pregnancy," *Science* 270:630-633 (1995).

Tanaka, J., et al., "Functional cell surface expression of toll-like receptor 9 promotes cell proliferation and survival in human hepatocellular carcinomas," *Int. J Oncol.*37:805-814 (2010).

Tel, J., et al., "Targeted delivery of CpG ODN to CD32 on human and monkey plasmacytoid dendritic cells augments 1FNα secretion," *Immunobiology* 217:1017-1024 (2012).

Tversky, J.R., et al., "Subcutaneous allergen immunotherapy restores human dendritic cell innate immune function," *Clin. Exp. Allergy.* 40(1):94-102 (2010).

Van Reijsen, F.C., et al., "Skin-derived aeroallergen-specific T-cell clones of Th2 phenotype in patients with atopic dermatitis," *J. Allergy Clin. Immunol.* 90:184-193 (1992).

Watson, S.A., et al., "Antibodies raised by Gastrimmune inhibit the spontaneous metastasis of a human colorectal tumour, AP5LV," *Eur J Cancer* 35(8):1286-1291 (1999).

Watson, S.A., et al., "Potential role of endocrine gastrin in the colonic adenoma carcinoma sequence," *British. J. Cancer* 87:567-573 (2002).

International Search Report, dated Aug. 5, 2014.

Cendron et al., Mol.lmmunol., 45 (2):307-319 (2008).

Office Action dated Feb. 26, 2018 in corresponding Japanese Patent Application No. 2016-514341.

Office Action dated Feb. 16, 2018 in corresponding Russian Patent Application No. 2015154795/10(084518).

\* cited by examiner

Fig. 3:

SEQ ID 1:

pEGPWLEEEEE AYGWMDF,

SEQ ID 2:

pEGPWLEEEEEAY

SEQ ID 3:

pEXPX

Wherein

X at position 2, 4 is any amino acid.

SEQ ID 4:

pEXPX

Wherein

X at position 2 is any of G or R;

X at position 4 is any of W or R

SEQ ID 5:

pEXPXXEEEEXAY

Wherein

X at position 2, 4, 5 or 10 is any amino acid.

Fig. 3 continued

SEQ ID 6:

pEXPXXEEEEXAY

Wherein

X at position 2 is any of G or R;

X at position 4 is any of W or R;

X at position 5 is any of L or M; and

X at position 10 is any of E or A.

SEQ ID 7:

pEXPXXEEEEXAYG

Wherein

X at position 2, 4, 5 or 10 is any amino acid.

SEQ ID 8:

pEXPXXEEEEXAYG

Wherein

X at position 2 is any of G or R;

X at position 4 is any of W or R;

X at position 5 is any of L or M; and

X at position 10 is any of E or A.

SEQ ID 9:

pEGPWLEEEEEAYG

SEQ ID 10:

p GPWLEEEEEAYG *GGSGG* KVSALKEKVSALKEKVSALKEKVSALKEKVSALKE bold is the peptide immunogen, *italic is linker*, underlined is coil

Fig. 3 continued

SEQ ID 11:

p GPWLEEEEEAYG*GG*
                |
                *KGGSGG*<u>KVSALKEKVSALKEKVSALKEKVSALKEKVSALKE</u>
                |
p GPWLEEEEEAYG*GG* bold is the peptide immunogen, *italic is linker*, <u>underlined is coil</u>

SEQ ID 12:

GGSGG

SEQ ID 13:

GG
  |
    KGGSGG
  |
GG

```
                        SEQUENCE LISTING

<160> NUMBER OF SEQ ID NOS: 57

<210> SEQ ID NO 1
<211> LENGTH: 17
<212> TYPE: PRT
<213> ORGANISM: Artificial Sequence
<220> FEATURE:
<223> OTHER INFORMATION: Peptide

<400> SEQUENCE: 1

Glu Gly Pro Trp Leu Glu Glu Glu Glu Ala Tyr Gly Trp Met Asp
1               5                   10                  15

Phe

<210> SEQ ID NO 2
<211> LENGTH: 12
<212> TYPE: PRT
<213> ORGANISM: Artificial Sequence
<220> FEATURE:
<223> OTHER INFORMATION: Peptide

<400> SEQUENCE: 2

Glu Gly Pro Trp Leu Glu Glu Glu Glu Glu Ala Tyr
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: 2
<223> OTHER INFORMATION: X is any amino acid
<220> FEATURE:
<221> NAME/KEY: PEPTIDE
<222> LOCATION: 4
<223> OTHER INFORMATION: X is any amino acid

<400> SEQUENCE: 3

Glu Xaa Pro Xaa
1

<210> SEQ ID NO 4
<211> LENGTH: 4
<212> TYPE: PRT
<213> ORGANISM: Artificial Sequence
<220> FEATURE:
```

```
<223> OTHER INFORMATION: Peptide
<220> FEATURE:
<221> NAME/KEY: PEPTIDE
<222> LOCATION: 2
<223> OTHER INFORMATION: X is any of G or R
<220> FEATURE:
<221> NAME/KEY: PEPTIDE
<222> LOCATION: 4
<223> OTHER INFORMATION: X is any of W or R

<400> SEQUENCE: 4

Glu Xaa Pro Xaa
1

<210> SEQ ID NO 5
<211> LENGTH: 12
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: 2
<223> OTHER INFORMATION: X is any amino acid
<220> FEATURE:
<221> NAME/KEY: PEPTIDE
<222> LOCATION: 4
<223> OTHER INFORMATION: X is any amino acid
<220> FEATURE:
<221> NAME/KEY: PEPTIDE
<222> LOCATION: 5
<223> OTHER INFORMATION: X is any amino acid
<220> FEATURE:
<221> NAME/KEY: PEPTIDE
<222> LOCATION: 10
<223> OTHER INFORMATION: X is any amino acid

<400> SEQUENCE: 5

Glu Xaa Pro Xaa Xaa Glu Glu Glu Glu Xaa Ala Tyr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: 2
<223> OTHER INFORMATION: X is any of G or R
<220> FEATURE:
<221> NAME/KEY: PEPTIDE
<222> LOCATION: 4
<223> OTHER INFORMATION: X is any of W or R
<220> FEATURE:
<221> NAME/KEY: PEPTIDE
<222> LOCATION: 5
<223> OTHER INFORMATION: X is any of L or M
<220> FEATURE:
<221> NAME/KEY: PEPTIDE
<222> LOCATION: 10
<223> OTHER INFORMATION: X is any of E or A

<400> SEQUENCE: 6

Glu Xaa Pro Xaa Xaa Glu Glu Glu Glu Xaa Ala Tyr
1               5                   10

<210> SEQ ID NO 7
<211> LENGTH: 13
<212> TYPE: PRT
<213> ORGANISM: Artificial Sequence
<220> FEATURE:
```

```
<223> OTHER INFORMATION: Peptide
<220> FEATURE:
<221> NAME/KEY: PEPTIDE
<222> LOCATION: 2
<223> OTHER INFORMATION: X is any amino acid
<220> FEATURE:
<221> NAME/KEY: PEPTIDE
<222> LOCATION: 4
<223> OTHER INFORMATION: X is any amino acid
<220> FEATURE:
<221> NAME/KEY: PEPTIDE
<222> LOCATION: 5
<223> OTHER INFORMATION: X is any amino acid
<220> FEATURE:
<221> NAME/KEY: PEPTIDE
<222> LOCATION: 10
<223> OTHER INFORMATION: X is any amino acid

<400> SEQUENCE: 7

Glu Xaa Pro Xaa Xaa Glu Glu Glu Glu Xaa Ala Tyr Gly
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: 2
<223> OTHER INFORMATION: X is any of G or R
<220> FEATURE:
<221> NAME/KEY: PEPTIDE
<222> LOCATION: 4
<223> OTHER INFORMATION: X is any of W or R
<220> FEATURE:
<221> NAME/KEY: PEPTIDE
<222> LOCATION: 5
<223> OTHER INFORMATION: X is any of L or M
<220> FEATURE:
<221> NAME/KEY: PEPTIDE
<222> LOCATION: 10
<223> OTHER INFORMATION: X is any of E or A

<400> SEQUENCE: 8

Glu Xaa Pro Xaa Xaa Glu Glu Glu Glu Xaa Ala Tyr Gly
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Peptide

<400> SEQUENCE: 9

Glu Gly Pro Trp Leu Glu Glu Glu Glu Glu Ala Tyr Gly
1               5                   10

<210> SEQ ID NO 10
<211> LENGTH: 53
<212> TYPE: PRT
<213> ORGANISM: Artificial Sequence
<220> FEATURE:
<223> OTHER INFORMATION: Immunogen-coil

<400> SEQUENCE: 10

Glu Gly Pro Trp Leu Glu Glu Glu Glu Glu Ala Tyr Gly Gly Gly Ser
1               5                   10                  15

Gly Gly Lys Val Ser Ala Leu Lys Glu Lys Val Ser Ala Leu Lys Glu
```

```
                    20                  25                  30

Lys Val Ser Ala Leu Lys Glu Lys Val Ser Ala Leu Lys Glu Lys Val
            35                  40                  45

Ser Ala Leu Lys Glu
    50

<210> SEQ ID NO 11
<211> LENGTH: 56
<212> TYPE: PRT
<213> ORGANISM: Artificial Sequence
<220> FEATURE:
<223> OTHER INFORMATION: Immunogen-coil
<220> FEATURE:
<221> NAME/KEY: PEPTIDE
<222> LOCATION: 16
<223> OTHER INFORMATION: Wherein the peptide of the sequence
      EGPWLEEEEEAYGGG is further linked via the C-terminal G to the K at
      position 16

<400> SEQUENCE: 11

Glu Gly Pro Trp Leu Glu Glu Glu Glu Ala Tyr Gly Gly Gly Lys
1               5                   10                  15

Gly Gly Ser Gly Gly Lys Val Ser Ala Leu Lys Glu Lys Val Ser Ala
            20                  25                  30

Leu Lys Glu Lys Val Ser Ala Leu Lys Glu Lys Val Ser Ala Leu Lys
        35                  40                  45

Glu Lys Val Ser Ala Leu Lys Glu
    50                  55

<210> SEQ ID NO 12
<211> LENGTH: 5
<212> TYPE: PRT
<213> ORGANISM: Artificial Sequence
<220> FEATURE:
<223> OTHER INFORMATION: Peptide

<400> SEQUENCE: 12

Gly Gly Ser Gly Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: 3
<223> OTHER INFORMATION: Wherein the peptide of the sequence GG is
      further linked via the C-terminal G to the K at position 3

<400> SEQUENCE: 13

Gly Gly Lys Gly Gly Ser Gly Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Peptide

<400> SEQUENCE: 14

Glu Val Ser Ala Leu
1               5
```

```
<210> SEQ ID NO 15
<211> LENGTH: 35
<212> TYPE: PRT
<213> ORGANISM: Artificial Sequence
<220> FEATURE:
<223> OTHER INFORMATION: Peptide

<400> SEQUENCE: 15

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Glu Val Ser Ala
            20                  25                  30

Leu Glu Lys
        35

<210> SEQ ID NO 16
<211> LENGTH: 5
<212> TYPE: PRT
<213> ORGANISM: Artificial Sequence
<220> FEATURE:
<223> OTHER INFORMATION: Peptide

<400> SEQUENCE: 16

Lys Val Ser Ala Leu
1               5

<210> SEQ ID NO 17
<211> LENGTH: 35
<212> TYPE: PRT
<213> ORGANISM: Artificial Sequence
<220> FEATURE:
<223> OTHER INFORMATION: Peptide

<400> SEQUENCE: 17

Lys Val Ser Ala Leu Lys Glu Lys Val Ser Ala Leu Lys Glu Lys Val
1               5                   10                  15

Ser Ala Leu Lys Glu Lys Val Ser Ala Leu Lys Glu Lys Val Ser Ala
            20                  25                  30

Leu Lys Glu
        35

<210> SEQ ID NO 18
<211> LENGTH: 5
<212> TYPE: PRT
<213> ORGANISM: Artificial Sequence
<220> FEATURE:
<223> OTHER INFORMATION: Peptide

<400> SEQUENCE: 18

Glu Ile Ala Ala Leu
1               5

<210> SEQ ID NO 19
<211> LENGTH: 21
<212> TYPE: PRT
<213> ORGANISM: Artificial Sequence
<220> FEATURE:
<223> OTHER INFORMATION: Peptide

<400> SEQUENCE: 19

Glu Ile Ala Ala Leu Glu Lys Glu Ile Ala Ala Leu Glu Lys Glu Ile
1               5                   10                  15

Ala Ala Leu Glu Lys
```

```
                        20

<210> SEQ ID NO 20
<211> LENGTH: 28
<212> TYPE: PRT
<213> ORGANISM: Artificial Sequence
<220> FEATURE:
<223> OTHER INFORMATION: Peptide

<400> SEQUENCE: 20

Glu Ile Ala Ala Leu Glu Lys Glu Ile Ala Ala Leu Glu Lys Glu Ile
1               5                   10                  15

Ala Ala Leu Glu Lys Glu Ile Ala Ala Leu Glu Lys
            20                  25

<210> SEQ ID NO 21
<211> LENGTH: 5
<212> TYPE: PRT
<213> ORGANISM: Artificial Sequence
<220> FEATURE:
<223> OTHER INFORMATION: Peptide

<400> SEQUENCE: 21

Lys Ile Ala Ala Leu
1               5

<210> SEQ ID NO 22
<211> LENGTH: 21
<212> TYPE: PRT
<213> ORGANISM: Artificial Sequence
<220> FEATURE:
<223> OTHER INFORMATION: Peptide

<400> SEQUENCE: 22

Lys Ile Ala Ala Leu Lys Glu Lys Ile Ala Ala Leu Lys Glu Lys Ile
1               5                   10                  15

Ala Ala Leu Lys Glu
            20

<210> SEQ ID NO 23
<211> LENGTH: 28
<212> TYPE: PRT
<213> ORGANISM: Artificial Sequence
<220> FEATURE:
<223> OTHER INFORMATION: Peptide

<400> SEQUENCE: 23

Lys Ile Ala Ala Leu Lys Glu Lys Ile Ala Ala Leu Lys Glu Lys Ile
1               5                   10                  15

Ala Ala Leu Lys Glu Lys Ile Ala Ala Leu Lys Glu
            20                  25

<210> SEQ ID NO 24
<211> LENGTH: 5
<212> TYPE: PRT
<213> ORGANISM: Artificial Sequence
<220> FEATURE:
<223> OTHER INFORMATION: Peptide

<400> SEQUENCE: 24

Glu Ile Ser Ala Leu
1               5

<210> SEQ ID NO 25
<211> LENGTH: 21
```

<212> TYPE: PRT
<213> ORGANISM: Artificial Sequence
<220> FEATURE:
<223> OTHER INFORMATION: Peptide

<400> SEQUENCE: 25

Glu Ile Ser Ala Leu Glu Lys Glu Ile Ser Ala Leu Glu Lys Glu Ile
1               5                   10                  15

Ser Ala Leu Glu Lys
            20

<210> SEQ ID NO 26
<211> LENGTH: 28
<212> TYPE: PRT
<213> ORGANISM: Artificial Sequence
<220> FEATURE:
<223> OTHER INFORMATION: Peptide

<400> SEQUENCE: 26

Glu Ile Ser Ala Leu Glu Lys Glu Ile Ser Ala Leu Glu Lys Glu Ile
1               5                   10                  15

Ser Ala Leu Glu Lys Glu Ile Ser Ala Leu Glu Lys
            20                  25

<210> SEQ ID NO 27
<211> LENGTH: 5
<212> TYPE: PRT
<213> ORGANISM: Artificial Sequence
<220> FEATURE:
<223> OTHER INFORMATION: Peptide

<400> SEQUENCE: 27

Lys Ile Ser Ala Leu
1               5

<210> SEQ ID NO 28
<211> LENGTH: 21
<212> TYPE: PRT
<213> ORGANISM: Artificial Sequence
<220> FEATURE:
<223> OTHER INFORMATION: Peptide

<400> SEQUENCE: 28

Lys Ile Ser Ala Leu Lys Glu Lys Ile Ser Ala Leu Lys Glu Lys Ile
1               5                   10                  15

Ser Ala Leu Lys Glu
            20

<210> SEQ ID NO 29
<211> LENGTH: 28
<212> TYPE: PRT
<213> ORGANISM: Artificial Sequence
<220> FEATURE:
<223> OTHER INFORMATION: Peptide

<400> SEQUENCE: 29

Lys Ile Ser Ala Leu Lys Glu Lys Ile Ser Ala Leu Lys Glu Lys Ile
1               5                   10                  15

Ser Ala Leu Lys Glu Lys Ile Ser Ala Leu Lys Glu
            20                  25

<210> SEQ ID NO 30
<211> LENGTH: 5
<212> TYPE: PRT
<213> ORGANISM: Artificial Sequence -continued

```
<220> FEATURE:
<223> OTHER INFORMATION: Peptide

<400> SEQUENCE: 30

Glu Val Ala Ala Leu
1               5

<210> SEQ ID NO 31
<211> LENGTH: 21
<212> TYPE: PRT
<213> ORGANISM: Artificial Sequence
<220> FEATURE:
<223> OTHER INFORMATION: Peptide

<400> SEQUENCE: 31

Glu Val Ala Ala Leu Glu Lys Glu Val Ala Ala Leu Glu Lys Glu Val
1               5                   10                  15

Ala Ala Leu Glu Lys
            20

<210> SEQ ID NO 32
<211> LENGTH: 28
<212> TYPE: PRT
<213> ORGANISM: Artificial Sequence
<220> FEATURE:
<223> OTHER INFORMATION: Peptide

<400> SEQUENCE: 32

Glu Val Ala Ala Leu Glu Lys Glu Val Ala Leu Glu Lys Glu Val
1               5                   10                  15

Ala Ala Leu Glu Lys Glu Val Ala Ala Leu Glu Lys
            20                  25

<210> SEQ ID NO 33
<211> LENGTH: 5
<212> TYPE: PRT
<213> ORGANISM: Artificial Sequence
<220> FEATURE:
<223> OTHER INFORMATION: Peptide

<400> SEQUENCE: 33

Lys Val Ala Ala Leu
1               5

<210> SEQ ID NO 34
<211> LENGTH: 21
<212> TYPE: PRT
<213> ORGANISM: Artificial Sequence
<220> FEATURE:
<223> OTHER INFORMATION: Peptide

<400> SEQUENCE: 34

Lys Val Ala Ala Leu Lys Glu Lys Val Ala Ala Leu Lys Glu Lys Val
1               5                   10                  15

Ala Ala Leu Lys Glu
            20

<210> SEQ ID NO 35
<211> LENGTH: 28
<212> TYPE: PRT
<213> ORGANISM: Artificial Sequence
<220> FEATURE:
<223> OTHER INFORMATION: Peptide

<400> SEQUENCE: 35
```

```
Lys Val Ala Ala Leu Lys Glu Lys Val Ala Leu Lys Glu Lys Val
1               5                   10                  15
Ala Ala Leu Lys Glu Lys Val Ala Ala Leu Lys Glu
            20                  25
```

<210> SEQ ID NO 36
<211> LENGTH: 21
<212> TYPE: PRT
<213> ORGANISM: Artificial Sequence
<220> FEATURE:
<223> OTHER INFORMATION: Peptide

<400> SEQUENCE: 36

```
Glu Val Ser Ala Leu Glu Lys Glu Val Ser Ala Leu Glu Lys Glu Val
1               5                   10                  15
Ser Ala Leu Glu Lys
            20
```

<210> SEQ ID NO 37
<211> LENGTH: 28
<212> TYPE: PRT
<213> ORGANISM: Artificial Sequence
<220> FEATURE:
<223> OTHER INFORMATION: Peptide

<400> SEQUENCE: 37

```
Glu Val Ser Ala Leu Glu Lys Glu Val Ser Ala Leu Glu Lys Glu Val
1               5                   10                  15
Ser Ala Leu Glu Lys Glu Val Ser Ala Leu Glu Lys
            20                  25
```

<210> SEQ ID NO 38
<211> LENGTH: 21
<212> TYPE: PRT
<213> ORGANISM: Artificial Sequence
<220> FEATURE:
<223> OTHER INFORMATION: Peptide

<400> SEQUENCE: 38

```
Lys Val Ser Ala Leu Lys Glu Lys Val Ser Ala Leu Lys Glu Lys Val
1               5                   10                  15
Ser Ala Leu Lys Glu
            20
```

<210> SEQ ID NO 39
<211> LENGTH: 28
<212> TYPE: PRT
<213> ORGANISM: Artificial Sequence
<220> FEATURE:
<223> OTHER INFORMATION: Peptide

<400> SEQUENCE: 39

```
Lys Val Ser Ala Leu Lys Glu Lys Val Ser Ala Leu Lys Glu Lys Val
1               5                   10                  15
Ser Ala Leu Lys Glu Lys Val Ser Ala Leu Lys Glu
            20                  25
```

<210> SEQ ID NO 40
<211> LENGTH: 297
<212> TYPE: PRT
<213> ORGANISM: Artificial Sequence
<220> FEATURE:
<223> OTHER INFORMATION: Peptide

<400> SEQUENCE: 40

```
Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
            35                  40                  45

Gly Trp Leu Asn Thr Tyr Thr Gly Glu Ser Ile Tyr Pro Asp Asp Phe
 50                  55                  60

Lys Gly Arg Phe Ala Phe Ser Ser Glu Thr Ser Ala Ser Thr Ala Tyr
 65                  70                  75                  80

Leu Gln Ile Asn Asn Leu Lys Asn Glu Asp Met Ala Thr Tyr Phe Cys
                 85                  90                  95

Ala Arg Gly Asp Tyr Gly Tyr Asp Asp Pro Leu Asp Tyr Trp Gly Gln
            100                 105                 110

Gly Thr Ser Val Thr Val Ser Gly Gly Gly Gly Ser Gly Gly Gly
            115                 120                 125

Gly Ser Gly Gly Gly Ser Asp Ile Val Met Thr Gln Ala Ala Pro
    130                 135                 140

Ser Val Pro Val Thr Pro Gly Glu Ser Val Ser Ile Ser Cys Arg Ser
145                 150                 155                 160

Ser Lys Ser Leu Leu His Thr Asn Gly Asn Thr Tyr Leu His Trp Phe
                165                 170                 175

Leu Gln Arg Pro Gly Gln Ser Pro Gln Leu Leu Ile Tyr Arg Met Ser
                180                 185                 190

Val Leu Ala Ser Gly Val Pro Asp Arg Phe Ser Gly Ser Gly Ser Gly
            195                 200                 205

Thr Ala Phe Thr Leu Ser Ile Ser Arg Val Glu Ala Glu Asp Val Gly
    210                 215                 220

Val Phe Tyr Cys Met Gln His Leu Glu Tyr Pro Leu Thr Phe Gly Ala
225                 230                 235                 240

Gly Thr Lys Leu Glu Leu Lys Gly Ser Ile Ser Ala Trp Ser His Pro
                245                 250                 255

Gln Phe Glu Lys Gly Pro Glu Val Ser Ala Leu Glu Lys Glu Val Ser
                260                 265                 270

Ala Leu Glu Lys Glu Val Ser Ala Leu Glu Lys Glu Val Ser Ala Leu
                275                 280                 285

Glu Lys Glu Val Ser Ala Leu Glu Lys
                290                 295

<210> SEQ ID NO 41
<211> LENGTH: 19
<212> TYPE: PRT
<213> ORGANISM: Artificial Sequence
<220> FEATURE:
<223> OTHER INFORMATION: Peptide

<400> SEQUENCE: 41

Ala Asp Gly Ala Trp Ala Trp Val Trp Leu Thr Glu Thr Ala Val Gly
1               5                   10                  15

Ala Ala Lys

<210> SEQ ID NO 42
<211> LENGTH: 249
<212> TYPE: PRT
<213> ORGANISM: Artificial Sequence
<220> FEATURE:
```

<223> OTHER INFORMATION: ScFV

<400> SEQUENCE: 42

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Gly Gly Gly Ser Gly Gly Gly
        115                 120                 125

Gly Ser Gly Gly Gly Ser Asp Ile Val Met Thr Gln Ala Ala Pro
    130                 135                 140

Ser Val Pro Val Thr Pro Gly Glu Ser Val Ser Ile Ser Cys Arg Ser
145                 150                 155                 160

Ser Lys Ser Leu Leu His Thr Asn Gly Asn Thr Tyr Leu His Trp Phe
                165                 170                 175

Leu Gln Arg Pro Gly Gln Ser Pro Gln Leu Leu Ile Tyr Arg Met Ser Val
            180                 185                 190

Leu Ala Ser Gly Val Pro Asp Arg Phe Ser Gly Ser Gly Ser Gly Thr
        195                 200                 205

Ala Phe Thr Leu Ser Ile Ser Arg Val Glu Ala Glu Asp Val Gly Val
    210                 215                 220

Phe Tyr Cys Met Gln His Leu Glu Tyr Pro Leu Thr Phe Gly Ala Gly
225                 230                 235                 240

Thr Lys Leu Glu Leu Lys Gly Ser Ile
                245

<210> SEQ ID NO 43
<211> LENGTH: 19
<212> TYPE: PRT
<213> ORGANISM: Artificial Sequence
<220> FEATURE:
<223> OTHER INFORMATION: Peptide

<400> SEQUENCE: 43

Ala Asp Gly Ala Trp Ala Trp Val Trp Leu Thr Glu Thr Ala Val Gly
1               5                   10                  15

Ala Ala Lys

<210> SEQ ID NO 44
<211> LENGTH: 248
<212> TYPE: PRT
<213> ORGANISM: Artificial Sequence
<220> FEATURE:
<223> OTHER INFORMATION: ScFV

<400> SEQUENCE: 44

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Lys Gly Leu Glu Trp Val
            35                  40                  45

Ala Glu Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Asn Asn
65                  70                  75                  80

Val Tyr Leu Gln Met Asn Asn Leu Arg Ala Glu Asp Thr Gly Ile Tyr
                85                  90                  95

Tyr Cys Asn Arg Arg Asp Glu Tyr Tyr Ala Met Asp Tyr Trp Gly Gln
            100                 105                 110

Gly Thr Ser Val Ser Val Ser Ser Gly Gly Gly Gly Ser Gly Gly Gly
            115                 120                 125

Gly Ser Gly Gly Gly Gly Ser Asp Ile Val Leu Thr Gln Ser Pro Gly
        130                 135                 140

Ser Leu Ala Val Ser Leu Gly Gln Arg Ala Thr Ile Ser Cys Arg Ala
145                 150                 155                 160

Ser Glu Ser Val Asp Asn Phe Gly Ile Ser Phe Met Asn Trp Phe Gln
                165                 170                 175

Gln Lys Pro Gly Gln Pro Arg Leu Leu Ile Tyr Gly Ala Ser Asn Gln
            180                 185                 190

Gly Ser Gly Val Pro Ala Arg Phe Ser Gly Ser Gly Ser Gly Thr Asp
        195                 200                 205

Phe Ser Leu Asn Ile His Pro Val Glu Glu Asp Asp Ala Ala Met Tyr
210                 215                 220

Phe Cys Gln Gln Ser Lys Glu Val Pro Trp Thr Phe Gly Gly Gly Thr
225                 230                 235                 240

Lys Leu Glu Ile Lys Gly Ser Ile
            245

<210> SEQ ID NO 45
<211> LENGTH: 229
<212> TYPE: PRT
<213> ORGANISM: Artificial Sequence
<220> FEATURE:
<223> OTHER INFORMATION: IgG1 Fc

<400> SEQUENCE: 45

Pro Lys Ser Cys Asp Lys Thr His Thr Cys Pro Pro Cys Pro Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
            35                  40                  45

Val Ser His Glu Asp Pro Glu Val Lys Phe Asn Trp Tyr Val Asp Gly
 50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
            115                 120                 125

Pro Gln Val Tyr Thr Leu Pro Pro Ser Arg Asp Glu Leu Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
            210                 215                 220

Leu Ser Pro Gly Lys
225

<210> SEQ ID NO 46
<211> LENGTH: 20
<212> TYPE: PRT
<213> ORGANISM: Artificial Sequence
<220> FEATURE:
<223> OTHER INFORMATION: Peptide

<400> SEQUENCE: 46

Gly Gly Gly Gly Gly Ala Cys Gly Ala Thr Cys Gly Thr Cys Gly Gly
1               5                   10                  15

Gly Gly Gly Gly
            20

<210> SEQ ID NO 47
<211> LENGTH: 24
<212> TYPE: PRT
<213> ORGANISM: Artificial Sequence
<220> FEATURE:
<223> OTHER INFORMATION: Peptide

<400> SEQUENCE: 47

Thr Cys Gly Thr Cys Gly Thr Thr Thr Gly Thr Cys Gly Thr
1               5                   10                  15

Thr Thr Gly Thr Cys Gly Thr Thr
            20

<210> SEQ ID NO 48
<211> LENGTH: 25
<212> TYPE: PRT
<213> ORGANISM: Artificial Sequence
<220> FEATURE:
<223> OTHER INFORMATION: Peptide

<400> SEQUENCE: 48

Thr Cys Gly Thr Cys Gly Thr Cys Gly Thr Cys Gly Ala Ala Cys
1               5                   10                  15

Gly Ala Cys Gly Thr Thr Gly Ala Thr
            20                  25

<210> SEQ ID NO 49
<211> LENGTH: 296
<212> TYPE: PRT
<213> ORGANISM: Artificial Sequence
<220> FEATURE:
<223> OTHER INFORMATION: ScFV-coil

<400> SEQUENCE: 49

```
Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
            35                  40                  45

Gly Trp Leu Asn Thr Tyr Thr Gly Glu Ser Ile Tyr Pro Asp Asp Phe
50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Gly Gly Gly Ser Gly Gly Gly
            115                 120                 125

Gly Ser Gly Gly Gly Ser Asp Ile Val Met Thr Gln Ala Ala Pro
        130                 135                 140

Ser Val Pro Val Thr Pro Gly Glu Ser Val Ser Ile Ser Cys Arg Ser
145                 150                 155                 160

Ser Lys Ser Leu Leu His Thr Asn Gly Asn Thr Tyr Leu His Trp Phe
                165                 170                 175

Leu Gln Arg Pro Gln Ser Pro Gln Leu Leu Ile Tyr Arg Met Ser Val
            180                 185                 190

Leu Ala Ser Gly Val Pro Asp Arg Phe Ser Gly Ser Gly Ser Gly Thr
        195                 200                 205

Ala Phe Thr Leu Ser Ile Ser Arg Val Glu Ala Glu Asp Val Gly Val
210                 215                 220

Phe Tyr Cys Met Gln His Leu Glu Tyr Pro Leu Thr Phe Gly Ala Gly
225                 230                 235                 240

Thr Lys Leu Glu Leu Lys Gly Ser Ile Ser Ala Trp Ser His Pro Gln
            245                 250                 255

Phe Glu Lys Gly Pro Glu Val Ser Ala Leu Glu Lys Glu Val Ser Ala
            260                 265                 270

Leu Glu Lys Glu Val Ser Ala Leu Glu Lys Glu Val Ser Ala Leu Glu
            275                 280                 285

Lys Glu Val Ser Ala Leu Glu Lys
            290                 295

<210> SEQ ID NO 50
<211> LENGTH: 294
<212> TYPE: PRT
<213> ORGANISM: Artificial Sequence
<220> FEATURE:
<223> OTHER INFORMATION: ScFV-coil

<400> SEQUENCE: 50

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Lys Gly Leu Glu Trp Val
            35                  40                  45

Ala Glu Ile Arg Leu Lys Ser Asn Asn Tyr Ala Thr His Tyr Ala Glu
50                  55                  60
```

```
Ser Val Lys Gly Arg Phe Thr Ile Ser Arg Asp Asp Ser Lys Asn Asn
 65                  70                  75                  80

Val Tyr Leu Gln Met Asn Asn Leu Arg Ala Glu Asp Thr Gly Ile Tyr
                 85                  90                  95

Tyr Cys Asn Arg Arg Asp Glu Tyr Tyr Ala Met Asp Tyr Trp Gly Gln
            100                 105                 110

Gly Thr Ser Val Ser Val Ser Ser Gly Gly Gly Gly Ser Gly Gly Gly
        115                 120                 125

Ser Gly Gly Gly Gly Ser Asp Ile Val Leu Thr Gln Ser Pro Gly Ser
    130                 135                 140

Leu Ala Val Ser Leu Gly Gln Arg Ala Thr Ile Ser Cys Arg Ala Ser
145                 150                 155                 160

Glu Ser Val Asp Asn Phe Gly Ile Ser Phe Met Asn Trp Phe Gln Gln
                165                 170                 175

Lys Pro Gly Gln Pro Pro Arg Leu Leu Ile Tyr Gly Ala Ser Asn Gln
            180                 185                 190

Gly Ser Gly Val Pro Ala Arg Phe Ser Gly Ser Gly Ser Gly Thr Asp
        195                 200                 205

Phe Ser Leu Asn Ile His Pro Val Glu Asp Ala Ala Met Tyr
210                 215                 220

Phe Cys Gln Gln Ser Lys Glu Val Pro Trp Thr Phe Gly Gly Gly Thr
225                 230                 235                 240

Lys Leu Glu Ile Lys Gly Ser Ile Ser Ala Trp Ser His Pro Phe Glu
                245                 250                 255

Lys Gly Pro Glu Val Ser Ala Leu Glu Lys Glu Val Ser Ala Leu Glu
            260                 265                 270

Lys Glu Val Ser Ala Leu Glu Lys Glu Val Ser Ala Leu Glu Lys Glu
        275                 280                 285

Val Ser Ala Leu Glu Lys
    290

<210> SEQ ID NO 51
<211> LENGTH: 56
<212> TYPE: PRT
<213> ORGANISM: Artificial Sequence
<220> FEATURE:
<223> OTHER INFORMATION: Peptide-coil

<400> SEQUENCE: 51

Ala Asp Gly Ala Trp Ala Trp Val Trp Leu Thr Glu Thr Ala Val Gly
 1               5                  10                  15

Ala Ala Lys Gly Pro Glu Val Ser Ala Leu Glu Lys Glu Val Ser Ala
                20                  25                  30

Leu Glu Lys Glu Val Ser Ala Leu Glu Lys Glu Val Ser Ala Leu Glu
            35                  40                  45

Lys Glu Val Ser Ala Leu Glu Lys
    50                  55

<210> SEQ ID NO 52
<211> LENGTH: 266
<212> TYPE: PRT
<213> ORGANISM: Artificial Sequence
<220> FEATURE:
<223> OTHER INFORMATION: IgG1 Fc-coil

<400> SEQUENCE: 52

Pro Lys Ser Cys Asp Lys Thr His Thr Cys Pro Pro Cys Pro Pro Glu
```

```
                1               5                   10                  15
            Leu Leu Gly Gly Pro Ser Val Phe Leu Phe Pro Pro Lys Pro Lys Asp
                            20                  25                  30

Thr Leu Met Ile Ser Arg Thr Pro Glu Val Thr Cys Val Val Val Asp
                            35                  40                  45

Val Ser His Glu Asp Pro Glu Val Lys Phe Asn Trp Tyr Val Asp Gly
                            50                  55                  60

Val Glu Val His Asn Ala Lys Thr Lys Pro Arg Glu Glu Gln Tyr Asn
             65                 70                  75                  80

Ser Thr Tyr Arg Val Val Ser Val Leu Thr Val Leu His Gln Asp Trp
                                85                  90                  95

Leu Asn Gly Lys Glu Tyr Lys Cys Lys Val Ser Asn Lys Ala Leu Pro
                            100                 105                 110

Ala Pro Ile Glu Lys Thr Ile Ser Lys Ala Lys Gly Gln Pro Arg Glu
                            115                 120                 125

Pro Gln Val Tyr Thr Leu Pro Pro Ser Arg Asp Glu Leu Thr Lys Asn
                130                 135                 140

Gln Val Ser Leu Thr Cys Leu Val Lys Gly Phe Tyr Pro Ser Asp Ile
            145                 150                 155                 160

Ala Val Glu Trp Glu Ser Asn Gly Gln Pro Glu Asn Asn Tyr Lys Thr
                            165                 170                 175

Thr Pro Pro Val Leu Asp Asp Gly Ser Phe Phe Leu Tyr Ser Lys Leu
                            180                 185                 190

Thr Val Asp Lys Ser Arg Trp Gln Gln Gly Asn Val Phe Ser Cys Ser
                            195                 200                 205

Val Met His Glu Ala Leu His Asn His Tyr Thr Gln Lys Ser Leu Ser
                210                 215                 220

Leu Ser Pro Gly Lys Gly Pro Glu Val Ser Ala Leu Glu Lys Glu Val
            225                 230                 235                 240

Ser Ala Leu Glu Lys Glu Val Ser Ala Leu Glu Lys Glu Val Ser Ala
                            245                 250                 255

Leu Glu Lys Glu Val Ser Ala Leu Glu Lys
                            260                 265

<210> SEQ ID NO 53
<211> LENGTH: 13
<212> TYPE: PRT
<213> ORGANISM: Artificial Sequence
<220> FEATURE:
<223> OTHER INFORMATION: Immunogen

<400> SEQUENCE: 53

Glu Gly Pro Trp Met Glu Glu Glu Glu Ala Ala Tyr Gly
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Immunogen

<400> SEQUENCE: 54

Glu Arg Pro Arg Met Glu Glu Glu Glu Ala Tyr Gly
1               5                   10

<210> SEQ ID NO 55
<211> LENGTH: 53
```

```
<212> TYPE: PRT
<213> ORGANISM: Artificial Sequence
<220> FEATURE:
<223> OTHER INFORMATION: Immunogen-coil

<400> SEQUENCE: 55

Glu Gly Pro Trp Met Glu Glu Glu Ala Ala Tyr Gly Gly Gly Ser
1               5                   10                  15

Gly Gly Lys Val Ser Ala Leu Lys Glu Lys Val Ser Ala Leu Lys Glu
            20                  25                  30

Lys Val Ser Ala Leu Lys Glu Lys Val Ser Ala Leu Lys Glu Lys Val
        35                  40                  45

Ser Ala Leu Lys Glu
    50

<210> SEQ ID NO 56
<211> LENGTH: 53
<212> TYPE: PRT
<213> ORGANISM: Artificial Sequence
<220> FEATURE:
<223> OTHER INFORMATION: Immunogen-coil

<400> SEQUENCE: 56

Glu Gly Pro Trp Leu Glu Glu Glu Glu Ala Tyr Gly Gly Gly Ser
1               5                   10                  15

Gly Gly Lys Val Ser Ala Leu Lys Glu Lys Val Ser Ala Leu Lys Glu
            20                  25                  30

Lys Val Ser Ala Leu Lys Glu Lys Val Ser Ala Leu Lys Glu Lys Val
        35                  40                  45

Ser Ala Leu Lys Glu
    50

<210> SEQ ID NO 57
<211> LENGTH: 57
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: 16
<223> OTHER INFORMATION: Wherein the peptide of the sequence
      EGPWMEEEEAAYGGG is further linked via the C-terminal G to the K at
      position 16

<400> SEQUENCE: 57

Pro Glu Gly Pro Trp Met Glu Glu Glu Ala Ala Tyr Gly Gly Gly
1               5                   10                  15

Lys Gly Gly Ser Gly Gly Lys Val Ser Ala Leu Lys Glu Lys Val Ser
            20                  25                  30

Ala Leu Lys Glu Lys Val Ser Ala Leu Lys Glu Lys Val Ser Ala Leu
        35                  40                  45

Lys Glu Lys Val Ser Ala Leu Lys Glu
    50                  55
```

GASTRIN PEPTIDE IMMUNOGENIC COMPOSITION

The invention refers to immunogenic compositions comprising a gastrin peptide immunogen and an anti-CD32 moiety linked to a TLR9 ligand, a vaccine comprising such immunogenic composition and its use in treating gastrin dependent disease conditions.

BACKGROUND

Cancer known medically as a malignant neoplasm, is a broad group of various diseases, all involving unregulated cell growth. In cancer, cells divide and grow uncontrollably, forming malignant tumors, and invade nearby parts of the body. The cancer may also spread to more distant parts of the body through the lymphatic system or bloodstream. Not all tumors are cancerous. Benign tumors do not grow uncontrollably, do not invade neighboring tissues, and do not spread throughout the body. There are over 200 different known cancers that afflict humans.

Determining what causes cancer is complex. Many things are known to increase the risk of cancer, including tobacco use, certain infections, radiation, lack of physical activity, obesity, and environmental pollutants. These can directly damage genes or combine with existing genetic faults within cells to cause the disease. Approximately five to ten percent of cancers are entirely hereditary.

Cancer can be detected in a number of ways, including the presence of certain signs and symptoms, screening tests, or medical imaging. Once a possible cancer is detected it is diagnosed by microscopic examination of a tissue sample. Cancer is usually treated with chemotherapy, radiation therapy and surgery. The chances of surviving the disease vary greatly by the type and location of the cancer and the extent of disease at the start of treatment. While cancer can affect people of all ages, and a few types of cancer are more common in children, the risk of developing cancer generally increases with age. In 2007, cancer caused about 13% of all human deaths worldwide (7.9 million). Rates are rising as more people live to an old age and as mass lifestyle changes occur in the developing world.

Since the immune system responds to the environmental factors it encounters on the basis of discrimination between self and non-self, many kinds of tumor cells that arise as a result of the onset of cancer are more or less tolerated by the patient's own immune system since the tumor cells are essentially the patient's own cells that are growing, dividing and spreading without proper regulatory control.

Immune tolerance or immunological tolerance is the process by which the immune system does not attack an antigen. In natural or self-tolerance, the body does not mount an immune response to self-antigens. It occurs in three forms: central tolerance, peripheral tolerance and acquired tolerance Central Tolerance[1]:

Central tolerance occurs during lymphocyte development and operates in the thymus and bone marrow. Here, T and B lymphocytes that recognize self-antigens are deleted before they develop into fully immunocompetent cells, preventing autoimmunity. This process is most active in fetal life, but continues throughout life as immature lymphocytes are generated.

Peripheral Tolerance[2]:

Peripheral tolerance is immunological tolerance developed after T and B cells mature and enter the periphery. The T cells that leave the thymus are relatively but not completely safe. Some will have receptors (TCRs) that can respond to self-antigens that are present in such high concentration that they can bind to "weak" receptors the T cell did not encounter in the thymus (such as, tissue-specific molecules like those in the islets of Langerhans, brain or spinal cord) Those self-reactive T cells that escape intrathymic negative selection in the thymus can inflict cell injury unless they are deleted or effectively muzzled in the peripheral tissue. Several feedback mechanism to silence such potentially auto reactive T cells are known to exist. They include following: Anergy, Activation-induced cell death, Peripheral suppression Acquired or Induced Tolerance[3]:

Acquired or induced tolerance refers to the immune system's adaptation to external antigens characterized by a specific non-reactivity of the lymphoid tissues to a given antigen that in other circumstances would likely induce cell-mediated or humoral immunity. One of the most important natural kinds of acquired tolerance is immune tolerance in pregnancy, where the fetus and the placenta must be tolerated by the maternal immune system.

Immunotherapy Targeting Tumor Associated Antigens:

Cancer immunotherapy is the use of the immune system to reject cancer. The main premise is stimulating the patient's immune system to attack the malignant tumor cells that are responsible for the disease. This can be either through active immunization of the patient (e.g., by administering a cellular cancer vaccine, such as Provenge, Dendreon, Seattle, Wash., US)[4], in which case the patient's own immune system is trained to recognize tumor cells as targets to be destroyed, or through the administration of therapeutic antibodies as drugs, in which case the patient's immune system is recruited to destroy tumor cells by the therapeutic antibodies. Another approach for activating the patient's immune system against tumors is to make use of so called tumor associated antigens (TAA's), which are self-proteins which are to some extend expressed on healthy normal cells, but overexpressed on tumor cells[5]. These TAAs are formulated and presented to the body in an immunogenic fashion such that the immune system will build a response despite the fact that these proteins are self. Obviously this approach will only be useful for TAAs against which the patient has developed peripheral or acquired tolerance. When the T and B cells recognizing the TAA have been deleted from the immunological repertoire, active cancer immunotherapy is not an option.

Gastrin:

An example of an autoantigen that may be used as target for treatment of gastro intestinal cancers such as pancreatic cancer is little gastrin (G17)[6-9]. In addition, neutralization of G17 may also be beneficial in any gastrin related disease condition, including gastric ulcers, Gastro Esophageal Reflux Disease (GERD)[10], since the pH of the stomach is regulated by gastrin, and for End Stage Renal Failure (ESRF)[11], since gastrin circulates at higher than normal concentrations in ESRF patients.

U.S. Pat. No. 5,023,077 describes immunogenic compositions and methods for the treatment and prevention of gastric and duodenal ulcer disease, which immunogenic compositions are based on gastrin peptides, which are coupled to an immunogenic carrier, such as diptheria toxoid, tetanus toxoid, keyhole limpet hemocyanin or bovine serum albumin.

Gastrin has several important functions in the gastrointestinal tract, the two most important being stimulation of acid secretion and stimulation of the growth of cells in the gastrointestinal tract. The hormone exists in at least two molecular forms, heptadecagastrin, the so-called little gastrin ("G17"), and tetratriacontagastrin ("G34") named according to the number of amino acid residues ("AA's") in each molecule, wherein the G17 constitutes the 17 amino terminal ("N-terminal") residues of G34.

U.S. Pat. No. 5,609,870 describes the preparation of an anti-G17 immunogen which raises antibodies in a mammal against its own G17 which do not react with G34 comprising conjugating a peptide which consists of a sequence corresponding to a fragment of the N-terminal amino acid sequence of G17 up to amino acid residue number 12 by its C-terminus to a spacer peptide which is conjugated to an immunogenic carrier, such as diphtheria toxoid, tetanus toxoid, keyhole limpet hemocyanin, and bovine serum albumin.

Immune Balance:

The immune balance regulated by Th1/Th2/Th17/Treg cells plays a significant part in the development of immune therapies.

Th1 cells, (Type 1 helper T cells) are characterized by the production of proinflammatory cytokines like IFN-γ, IL-2, and TNF-β. Th1 cells are involved in cell-mediated immunity. The cytokines produced by Th1 cells stimulate the phagocytosis and destruction of microbial pathogens. Several chronic inflammatory diseases have been described as Th1 dominant diseases i.e. multiple sclerosis, diabetes, and rheumatoid arthritis.

Th2 cells (Type 2 helper T cells) are characterized by the production of IL-4, IL-5, IL-9, IL-10, and IL-13. Th2 cells are thought to play a role in allergy responses. Cytokines like IL-4 generally stimulate the production of antibodies. IL-5 stimulates eosinophil responses, also part of the immune response. Atopy and allergy are thought to be Th2 dominant conditions.

The imbalance of Th1/Th2 or Th17/Treg immunity becomes the cause of various immune diseases.

Allergy is considered to be a hypersensitive reaction to proteins in the environment. Allergens are antigens to which atopic patients respond with IgE antibody responses subsequently leading to allergic reactions. Antigens in the complexes or fusion proteins can be environmental allergens (e.g. house dust mite, birch pollen, grass pollen, cat antigens, cockroach antigens), or food allergens (e.g. cow milk, peanut, shrimp, soya), or a combination of both. IgE molecules are important because of their role in effector cell (mast cell, basophiles and eosinophiles) activation. It is generally accepted that IgE also plays an important role in the induction phase of allergic diseases, by up-regulating the antigen capture potential of B cells and dendritic cells (DC), both through low affinity (CD23) and high affinity receptors (FcεRI). The negative functions of IgE antibodies can be counteracted by allergen specific IgG antibodies e.g., because they direct the immune response away from B cells to monocytes and DC. In addition, they compete with IgE molecules for allergen binding sites. Allergies therefore can be treated, cured and prevented by the induction of allergen specific IgG molecules.

IgG molecules have a serum half-life of approximately three weeks as compared to roughly three days for IgE molecules. IgE molecules are induced by the interaction between (naïve) B cells and Th2 cells which provide the IL-4 and IL-13 together with CD40L expression necessary to induce a class switch to IgE in memory B cells and plasma cells. In contrast, Th1 cells, which produce IFN-γ and IL-2, induce a class switch to IgG. Therefore, induction of Th1, rather than Th2 helper T cell responses against allergens, is beneficial for the prevention, treatment and cure of allergic diseases.

In WO 97/07218 Allergen-anti-CD32 Fusion Proteins are described. In this publication the problems with isolating specific IgG molecules and the low affinity of these IgG antibodies for CD32 are circumvented and the risk factors of classical immunotherapy, which uses complete "IgE binding" allergens, are reduced.

WO2007098934A1 describes molecules capable of binding to TLR9 and to CD32 comprising at least one epitope of at least one antigen, its production and its use in a medicament, especially for the treatment of allergies.

The Role of TLR9:

Toll-like receptors (TLRs) are a class of proteins that play a key role in the innate immune system. They are single, membrane-spanning, non-catalytic receptors usually expressed on the cell surface and in the endocytic compartment of sentinel cells such as macrophages and dendritic cells. TLR's recognize pathogen-associated molecular patterns (PAMPs), structurally conserved molecules, derived from microbes and initiate signalling to induce production of cytokines necessary for the innate immunity and subsequent adaptive immunity.

The various TLRs exhibit different patterns of expression. This gene is preferentially expressed in immune cell rich tissues, such as spleen, lymph node, bone marrow and peripheral blood leukocytes.

Thirteen TLRs (named simply TLR1 to TLR13) have been identified in humans and mice together, and equivalent forms of many of these have been found in other mammalian species. However, not every TLR receptor in mice is also found in humans or vice versa. In addition, not for every TLR receptor the ligand and function is known, e.g. TLR10 is orphan receptor with unknown function.

Activation of TLR receptors has been used for the treatment of various diseases e.g. activation of TLR9 by pharmaceutical products has been shown to be beneficial in treatment of allergy and oncology. Studies in mice and human indicate that the natural ligands of TLR9 are unmethylated CpG sequences in DNA molecules. CpG sites are relatively rare (~1%) on vertebrate genomes in comparison to bacterial genomes or viral DNA. TLR9 is expressed by numerous cells of the immune system such as dendritic cells, B lymphocytes, monocytes and natural killer (NK) cells. However in healthy humans the TLR9 is expression is restricted to plasmacytoid dendritic cells (pDCs) and B cells. The expression is intracellularly, within the endosomal compartments and functions to alert the immune system of viral and bacterial infections by binding to DNA rich in CpG motifs. However under pathologiocal conditions TLR9 expression has been reported on the cell surface of cells as well[12-14].

Many different synthetic TLR9 agonist molecules have been reported. The agonistic ligands (TLR9 activating) have been classified into three groups:

The group consisting of CpG class A, in particular CpG-A (D)[15] oligodeoxynucleotides (ODN), also known as "D"-type ODN. Such TLR9 agonists induce a strong IFNa induction and minimal maturation of dendritic cells, and are herein called "group 1" TLR9 ligand. An example is ODN2216[16]:

(SEQ ID 46)
GGGGGACGATCGTCGGGGGG

The group consisting of CpG class B, in particular CpG-B (K)[15] oligodeoxynucleotides (ODN), also known as "K"-type ODN. Such TLR9 agonists induce a weak IFNa induction and maturation of dendritic cells, and are herein called "group 2" TLR9 ligand. An example is ODN2006[17;18]:

TCGTCGTTTTGTCGTTTTGTCGTT (SEQ ID 47)

The group consisting of CpG class C, also known as CpG-C[15] oligodeoxynucleotides (ODN). Such TLR9 agonists induce IFNa and maturation of immature dendritic cells, and are herein called "group 3" TLR9 ligand. An example is ODNM362[15]:

TCGTCGTCGTTCGAACGACGTTGAT (SEQ ID 48)

All of the ligands for TLR9 described to date are based on nucleotides. Although antibodies specific for TLR9 have been reported and used to demonstrate the presence and location of the receptor, these molecules have not been described as ligands for TLR9, there was no report of any TLR9 activating or inhibiting activity.

The Role of CD32:

CD32 is strongly expressed on monocytes/dendritic cells and B cells and thus such molecules are designed to direct the immune response to these important immunological cells, with the intention to prevent antigen presentation by the B cells, while promoting antigen presentation by especially dendritic cells (DCs), the latter leads to induction of Th1 responses against the antigen, when sufficiently stimulated. There are at least two types of DCs: myeloid (mDC) and plasmacytoid dendritic cells (pDC), which has led to the new concept of DC1 and DC2 cells. In this concept DC1 cells promote the induction of Th1 cell development after antigen specific stimulation and DC2 cells support the development of Th2 cells. Monocyte derived DC (or mDC) are generally considered to be of DC1 type, whereas pDC are considered to be DC2 type. Both types of DC express CD32a and will induce an antigen specific T cell response; however it is not guaranteed that the outcome will be of Th1 type. In fact, in allergic donors Th2 responses are more likely. Importantly, the pDC express the TLR9 receptor, which binds CpG-ODNs (oligodeoxynucleotides (ODNs) containing unmethylated CpG motifs). Activation of this receptor in the pDC leads to a very strong production of IFN-alpha and IL-12, which promotes Th1 induction and thus transforms the potential DC2 into DC1 cells.

Thus, such molecules can combine the activation of the TLR9 receptor in pDC with the specific stimulation and induction of antigen specific Th1 cells.

In tumor immunotherapies there is the particular goal to use tumor antigen specific T helper type 1 (Th1) cells in addition to cytotoxic T lymphocytes (CTL).

Coiled Coils:

Coiled coils are consisting of structural motifs in proteins, in which 2-7 alpha-helices are coiled together like the strands of a rope; dimers and trimers are the most common types. The coiled coil helixes have been used to stabilize Fv antibody fragments resulting in heterodimeric coiled-coil domains[19].

SUMMARY OF THE INVENTION

There is a need to provide improved immunotherapies targeting gastrin and gastrin dependent disease conditions. It is thus the object of the invention to provide a vaccine with improved immunogenicity, stability and structure to regulate the immune response to specific gastrin epitopes.

The object is solved by the subject matter as claimed.

According to the invention there is provided an immunogenic composition comprising a. a directed adjuvant comprising at least an anti-CD32 moiety linked to a TLR9 ligand and a first peptidic alpha-helix; and b. a gastrin-17 peptide immunogen linked to a second peptidic alpha-helix coiled to the first alpha-helix, which peptide immunogen is any of (i) human gastrin-17 comprising the amino acid sequence of SEQ ID 1, or a fragment thereof comprising the amino acid sequence of SEQ ID 2, or at least the 4 N-terminal amino acids of SEQ ID 2;

(ii) an analog of (i), preferably of rhesus monkey or murine origin; and/or (iii) a functionally active variant of any of (i) or (ii), with one, two, three or four point mutations in the amino acid sequence of SEQ ID 2.

Specifically, said peptide immunogen is a linear peptide comprising or consisting of (i) an amino acid sequence of SEQ ID 3, preferably SEQ ID 4;

(ii) an amino acid sequence of SEQ ID 5, preferably SEQ ID 6;

(iii) an amino acid sequence of SEQ ID 7, preferably SEQ ID 8; or (iii) an amino acid sequence of SEQ ID 2 or 9.

It is preferred that the immunogenic composition of the invention comprises at least two of the peptide immunogens linked to the second peptidic alpha-helix, preferably 2, 3 or 4 of the peptide immunogens.

When more than one peptide immunogens are bound to the second alpha-helix, the peptide immunogens may e.g. be conjugated to the alpha-helix consecutively, i.e. linking the peptide imunogens in a row, e.g. linking the C-terminus of a first peptide immunogen to an N-terminus of a second peptide immunogen, which first and second peptide immunogens are identical or differ from each other.

Alternatively, or in addition, further peptide immunogens may be incorporated into the immunogenic composition of the invention by cross-linking e.g. two or more peptide immunogens, which are either identical or differ from each other, are linked to the same alpha-helix by chemical reaction, such as chemical cross-linking permitting the establishment of inter-molecular cross-linkages, e.g. with homo-bifunctional reagents such as Dimethyl adipimidate (DMA), Dimethyl suberimidate (DMS), or glutaraldehyde. For example, such cross-linking may be performed employing glutaraldehyde crosslinking by free lysine groups of the alpha-helix or a spacer/linker, respectively. Thereby, two or more peptide immunogens as used according to the invention are coupled to the alpha-helix in parallel, or side-by-side.

According to a specific aspect of the invention, each of said first and second alpha-helices comprises 3-5 amino acid repeats of an amino acid motive, specifically binding to each other with a Kd of less than $10^{-6}$ M, preferably with a Kd of less than $10^{-7}$ M, more preferred less than $10^{-8}$ M or $10^{-9}$ M.

According to a further specific aspect of the invention, said anti-CD32 moiety is selected from the group consisting of an anti-CD32 antibody, an antibody fragment and a peptide, preferably targeting CD32a. The antibody fragment specifically may e.g. be an Fab, Fv, scFv, dAb, F(ab)2 or Fcab fragment, or any other possible binding entity, as long as it specifically binds to the receptor and is internalized after binding.

Specifically said anti-CD32 moiety is targeting CD32a, preferably with a high affinity of Kd $10^{-6}$ M, more preferred less than $10^{-7}$ M or less than $10^{-8}$ M.

More specifically said anti-CD32 moiety is a specific or selective CD32a binder, i.e. not targeting CD32b or targeting CD32b with a low affinity of Kd>$10^{-6}$ M, preferably higher than $10^{-5}$ M, more preferred higher than $10^{-4}$ M. The differential affinity of binding to CD32a and CD32b is preferably at least 1 log, more preferred at least 2 logs or at least 3 logs of higher difference in the Kd value.

The specifically preferred high affinity or high differential affinity of the anti-CD32 moiety to bind CD32a rather than CD32b is typically used in an immunostimulating vaccine further employing the agonistic TLR9 ligand.

Binding affinity of the anti-CD32 moiety targeting specifically any of CD32a or CD32b, or both, CD32a and CD32b, can be determined in a suitable assay such as a typical ELISA using commercially available HIS-tagged recombinant forms of CD32a and CD32b, coated to Ni-NTA ELISA plates, e.g. Ni-NTA HisSorb Plates (Qiagen, Austria). The anti-CD32 moieties may be biotinylated and as such may be detected using streptavidine-HRP or streptavidine AP and the appropriate substrates. Alternatively the moieties may be tested in a FACS assay using U937 cells (e.g. ATCC: CRL 1593) expressing CD32a but not CD32b and EBV transformed B cells e.g. CFB4:2 as described by van Reijsen et al[20], expressing CD32b and not CD32a According to a further specific aspect of the invention, said TLR9 ligand is a TLR9 agonist selected from the group consisting of CpG oligodeoxynucleotides class A, B and C, or an immunostimulatory peptide mimicking any of the CpG oligodeoxynucleotides.

According to a specific aspect of the invention, the TLR9 ligand is a TLR9 agonist selected from the group consisting of CpG class A, in particular CpG-A (D)[17] oligodeoxynucleotides (ODN), also known as "D"-type ODN. Such TLR9 agonists induce a strong IFNa induction and minimal maturation of dendritic cells, and are herein called "group 1" TLR9 ligand.

According to another specific aspect of the invention, the TLR9 ligand is a TLR9 agonist selected from the group consisting of CpG class B, in particular CpG-B (K)[21] oligodeoxynucleotides (ODN), also known as "K"-type ODN. Such TLR9 agonists induce a weak IFNa induction and maturation of dendritic cells, and are herein called "group 2" TLR9 ligand.

According to another specific aspect of the invention, the TLR9 ligand specifically is a TLR9 agonist selected from the group consisting of CpG class C, also known as CpG-C[15;21] oligodeoxynucleotides (ODN). Such TLR9 agonists induce IFNa and maturation of immature dendritic cells, and are herein called "group 3" TLR9 ligand.

The induction of IFNa may be determined by the level of IFNa expression and the respective increase with respect to a reference level. The increase relative to non-stimulated cells may be compared to the induction levels induced by established references for each type of CpG as defined by group 1, 2 or 3 TLR9 ligand and is typically between 30% and 300% of the respective reference, preferably at least 100%, more preferably at least 120%, at least 150%, at least 200% or at least 250%.

The maturation of immature dendritic cells may be determined by the level of expression of any of the markers CD80, CD83 and CD86. The respective increase relative to non-stimulated cells may be compared to the induction levels induced by established references for each type of CpG as defined by group 1, 2 or 3 TLR9 ligand and is typically between 30% and 300% of the respective reference, preferably at least 100%, more preferably at least 120%, at least 150%, at least 200% or at least 250%.

Specifically, the TLR9 agonist of group 1 and 3 would result in an increased IFNa expression and a TRL9 agonist of group 2 and 3 would lead to an increased expression of any of the DC maturation factors CD80, CD83 and CD86. The TLR9 antagonist would result in a reduced IFNa expression and a reduced expression of any of the DC maturation factors CD80, CD83 and CD86, even in the presence of a TLR9 agonist of either group 1-3.

As an alternative to the polynucleotide TLR9 ligands as described above, any other TLR9 binder with agonistic effect may be used, e.g. a peptide binder or protein binder, including antibodies or antibody fragments.

According to a further specific aspect of the invention, the immunogenic composition comprises one or more linker sequences, preferably composed of glycine and/or serine and/or lysine residues, preferably an amino acid sequence of SEQ ID 12 or 13. The linker sequences may be linear or branched, e.g. to provide linkage or cross-linkage between two or more peptide or polyeptide entities.

According to a further specific aspect of the invention, the immunogenic composition comprises or consists of the amino acid sequence of SEQ ID 10 or SEQ ID 11.

According to the invention, there is further provided a vaccine comprising the immunogenic composition of the invention, and a pharmaceutically acceptable carrier. Such vaccine is typically an immunostimulating vaccine, e.g. stimulating the humoral and T-cell (Th1) immune response.

According to a preferred embodiment, the humoral and T-cell (Th1) immune response is transient, e.g. with a specific maximum IgG titer induced upon vaccination that is typically achieved within a period of 2 to 8 weeks upon vaccination, followed by a titer reduction by at least 30%, preferably at least 40%, or at least 50%, or at least 60%, or at least 70%, or at least 80%, or at least 90%, or up to 100%, within 6 months upon vaccination, preferably within 5 months, or within 4 months, or within 3 months, or within 2 months. Such reduced titer may be again increased upon a booster injection. In a series of vaccination, the transient immune response is possibly determined upon the last injection of the immunogenic composition or vaccine. The transient immune response has the advantage of a controlled treatment with, e.g. the possibility to interrupt or stop treatment as necessary.

According to the invention, there is further provided a kit for preparing the immunogenic composition of the invention, comprising the following components a. a directed adjuvant comprising at least an anti-CD32 moiety linked to a TLR9 ligand and a first peptidic alpha-helix; and b. a gastrin-17 peptide immunogen linked to a second peptidic alpha-helix matching the first alpha-helix, which peptide immunogen is any of (i) human gastrin-17 comprising the amino acid sequence of SEQ ID 1, or a fragment thereof comprising the amino acid sequence of SEQ ID 2, or at least the 4 N-terminal amino acids of SEQ ID 2;

(ii) an analog of (i), preferably of rhesus monkey or murine origin; and/or (iii) a functionally active variant of any of (i) or (ii), with one, two, three or four point mutations in the amino acid sequence of SEQ ID 2.

The kit may specifically be used to facilitate the production of the vaccine by using the preformed directed adjuvant component for the combination with an immunogen that may be provided according to the need of a subject group or the individual subject.

According to the invention, there is further provided the immunogenic composition for use in treating a subject suffering from gastrin dependent diseases or disease conditions. Such disease or disease condition is primarily caused by or associated with the endogenous gastrin production or over-production in the subject. The gastrin dependent diseases or disease conditions specifically include gastrin dependent tumors or gastrin dependent cancer, such as pancreatic cancer, or gastrointestinal cancers, gastric ulcer, gastroesophageal reflux disease (GERD), end-stage renal failure (ESRF), or obesity.

Thus, the invention specifically provides for a method of treating a subject suffering from gastrin dependent diseases, such as gastrin dependent tumors or gastrin dependent cancer, such as pancreatic cancer, or gastrointestinal cancers, gastric ulcer, gastroesophageal reflux disease (GERD), end-stage renal failure (ESRF), or obesity, by administering to the subject an effective amount of the immunogenic composition or the vaccine of the invention, either prophylactically, e.g. to prevent the outbreak of a disease or disease condition or the progress of disease, or therapeutically, e.g. to ameliorate a disease or disease condition.

Specifically, the composition is administered to the subject in an effective amount employing a prime-boost strategy.

Specifically, the effective amount is ranging between 0.0001 and 2 mg per administration, preferably between 0.001 and 2 mg per dose.

According to a specific embodiment of the invention, the subject is further treated by chemotherapy, e.g. in the course of treating a gastrin dependent cancer.

Specifically, the immunogenic composition of the invention triggers a protective immune response in the subject, preferably with a serum IgG titer against human gastrin-17 of at least $1/1000$, preferably at least $1/10^4$, preferably at least $1/10^5$, preferably at least $1/10^6$, or lower, thus, detectable at a higher dilution.

FIGURES

Figure 2:
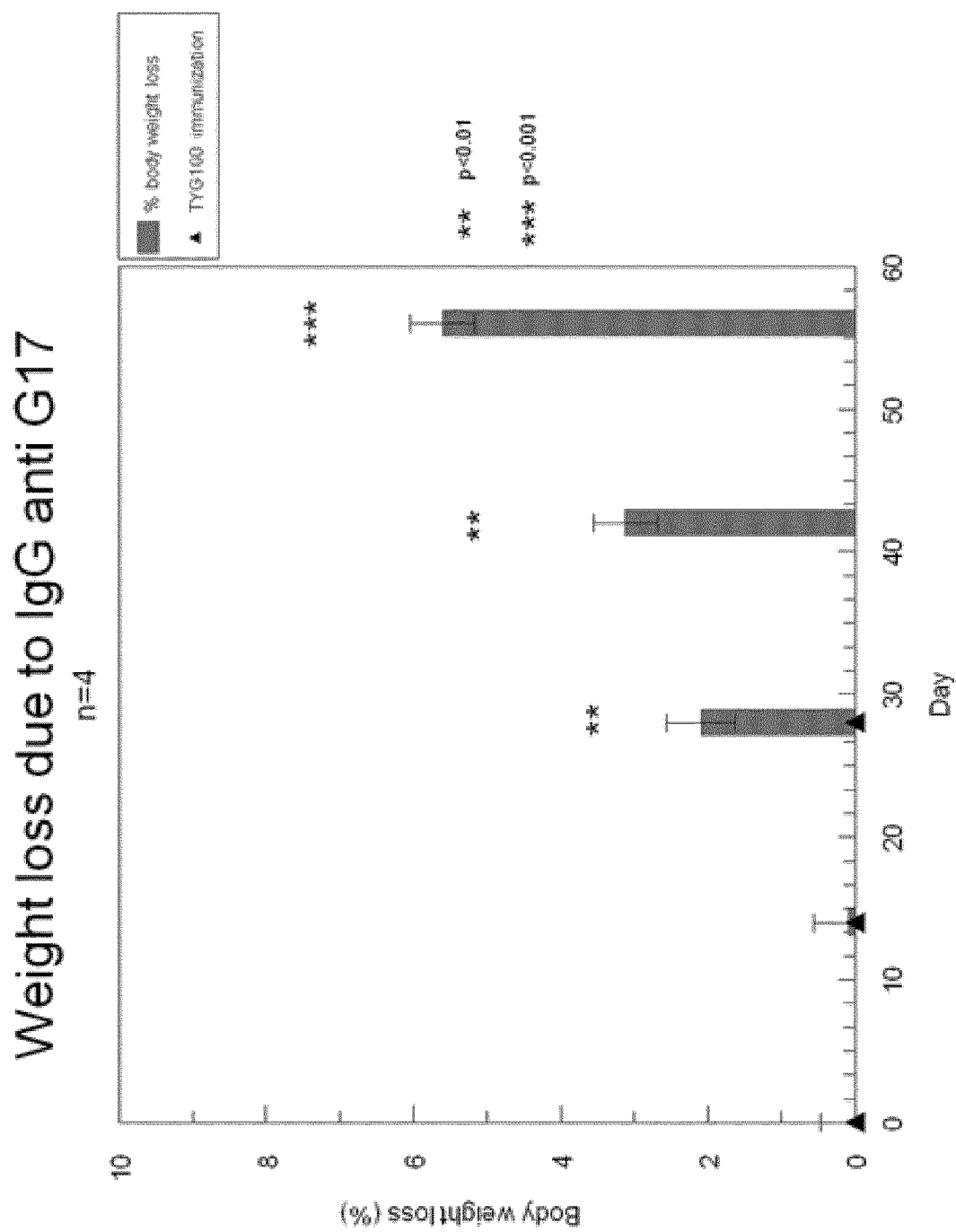

FIG. 1 shows the antibody (IgG induction) in cynomolgus monkeys. Time curve IgG anti G17 induction, after three injections with the vaccine (TYG100_2RM) on d0, d14 and d28. A significant IgG induction was seen against the ScFV-coil1 and G17RM and G17H. No response was seen against a control peptide of similar molecular weight or when the animals were immunized with G17RM_2 without the presence of warhead. All specific IgG titers decline 4 weeks after last immunization indicating that booster injections are necessary to maintain the IgG levels. In addition, the presence of natural G17RM does not boost the response and since the decrease in IgG against G17RM is significantly higher than the one for ScFV-coil1, it may be concluded that the induced immune response is reversible FIG. 2 shows the weight loss upon anti-gastrin immunization. Four out of 6 animals showed a significant time dependent weight loss after immunization with TYG100_2RM. It was observed by the animal care takers that these animals lost appetite for their afternoon snacks, without losing interest in normal daily food. Such observations were never made with other vaccines, therefore the anti-gastrin vaccine of the invention can be used to control obesity.

FIG. 3 shows the sequence information of

SEQ ID 1: human little gastrin, G17;

SEQ ID 2: human gastrin peptide, first (N-terminal) 12 AA (amino acids) of little gastrin, G12;

SEQ ID 3: N-terminal epitope of little gastrin, first (N-terminal) 4 AA, including specific functionally active variants with point mutations;

SEQ ID 4: N-terminal epitope of little gastrin, first (N-terminal) 4 AA, including more specific functionally active variants with point mutations;

SEQ ID 5: N-terminal epitope of little gastrin, first (N-terminal) 12 AA, including specific functionally active variants with point mutations;

SEQ ID 6: N-terminal epitope of little gastrin, first (N-terminal) 12 AA, including more specific functionally active variants with point mutations;

SEQ ID 7: N-terminal epitope of little gastrin, first (N-terminal) 13 AA, including specific functionally active variants with point mutations;

SEQ ID 8: N-terminal epitope of little gastrin, first (N-terminal) 13 AA, including more specific functionally active variants with point mutations;

SEQ ID 9: human gastrin peptide, first (N-terminal) 13 AA (amino acids) of little gastrin, G13;

SEQ ID 10: Immunogen component of TYG100_1H: Part of an immunogenic composition of the invention, comprising one human gastrin peptide of SEQ ID 9, a linker sequence and a peptide alpha-helix (TYG100_1H). This part may be linked to the suitable directed adjuvant by a coiled-coil linkage.

bold is the peptide immunogen, italic is linker, underlined is coil

SEQ ID 11: Immunogen component of TYG100_2H: Part of an immunogenic composition of the invention, comprising two human gastrin peptides of SEQ ID 9, a branched linker sequence and a peptide alpha-helix (TYG100_2H). This part may be linked to the suitable directed adjuvant by a coiled-coil linkage.

bold is the peptide immunogen, italic is linker, underlined is coil

SEQ ID 12: linear linker sequence;

SEQ ID 13: branched linker sequence.

DETAILED DESCRIPTION OF THE INVENTION

Specific terms as used throughout the specification have the following meaning.

The term "adjuvant" as used herein shall mean an integrated or co-administered component of a vaccine, which:

enhances the immune response to a specific immunogen, e.g. an antigen or a hapten. The immune response is typically greater than the immune response elicited by an equivalent amount of the immunogenic composition administered without the adjuvant, and/or the adjuvant is used to direct a particular type or class of immune response against the immunogen, e.g. a Th1 or Treg type of immune response, herein understood as "directed adjuvant".

An "effective amount" of an adjuvant of the present invention specifically is an amount which enhances an immunological response to the immunogen such that, for example, lower or fewer doses of the immunogenic composition are required to generate an efficient immune response of the intended class.

The directed adjuvant according to the invention not only mediates the efficient immune response, but also the regulation of the immune response in the desired way. By directing the immunogen to the appropriate immune cells for its internalization and further processing, the Th1 immune response is induced rather than the Th2 immune response, in particular when employing a TLR9 ligand that is a TLR9 agonist of group 3. If a TLR9 agonist of group 1 is combined with an anti-CD32 moiety that binds CD32b, the induction of Treg cells is usually anticipated.

An "effective amount" of an immunogenic composition, e.g. as used in a vaccine of the invention refers to an amount sufficient to show a meaningful benefit in a subject being treated, when administered as part of a vaccination dosing regimen. Those of ordinary skill in the art will appreciate that, in some embodiments, a particular composition may be considered to contain a prophylactically or therapeutically effective amount if it contains an amount appropriate for a unit dosage form administered in a specific dosing regimen, even though such amount may be insufficient to achieve the meaningful benefit if administered as a single unit dose. Those of ordinary skill will further appreciate that an effective amount of an immunogenic composition may differ for different subjects receiving the composition, for example depending on such factors as the desired biological endpoint, the nature of the composition, the route of administration, the health, size and/or age of the subject being treated, etc. In some embodiments, a effective amount is one that has been correlated with beneficial effect when administered as part of a particular dosing regimen, e.g. a single administration or a series of administrations such as in a "boosting" regimen.

The term "peptidic alpha-helix" as used herein shall mean a coiled structural motif based on a peptide sequence comprising a number of repeats, also called coil repeats. Such alpha-helix is capable of binding to another counterpart, also called matching alpha-helix of the same type to form a dimer, trimer or further oligomer, also called coiled coil.

A coiled coil is a structural motif in polypeptides or peptides, in which two to seven alpha-helices are coiled together like the strands of a rope. In some embodiments, the coiled coil of the vaccine is one with two alpha-helices coiled together. Such alpha helical regions are likely to form coiled-coil structures and may be involved in oligomerization of the coil repeats as measured in a suitable coiled coil interaction binding assay.

Specifically a dimer of alpha-helices can be formed by contacting the two monomers, such that the dimer is formed through an interaction with the two alpha helix coiled coil domains. In some embodiments the coils comprise a peptide with the amino acid sequence as set forth in SEQ ID NO: 14 or 16 (coil and anti-coil), which include x repeats.

```
E5:
                                                    (SEQ ID 14)
    EVSAL (SEQ ID 15)
    EVSALEKEVSALEKEVSALEKEVSALEKEVSALEK-NH2

K5:
                                                    (SEQ ID 16)
    KVSAL (SEQ ID 17)
    KVSALKEKVSALKEKVSALKEKVSALKEKVSALKE-NH2
```

Alternatively, any of the sequences described by Chao et al[22] or Litowsky et al[23;24] or functional equivalents, which generate the specific coiled-coil type linkage, may be used, such as indicated in the following table, including variants thereof, e.g. with a different number of repeats, or one, two or three point mutations in the coil type:

| Coil Type | Type/number of repeats: Exemplary sequence |
| --- | --- |
| EIAAL (SEQ ID 18) | E3: EIAALEKEIAALEKEIAALEK-NH2 (SEQ ID 19) |
| EIAAL (SEQ ID 18) | E4: EIAALEKEIAALEKEIAALEKEIAALEK-NH2 (SEQ ID 20) |
| KIAAL (SEQ ID 21) | K3: KIAALKEKIAALKEKIAALKE-NH2 (SEQ ID 22) |
| KIAAL (SEQ ID 21) | K4: KIAALKEKIAALKEKIAALKEKIAALKE-NH2 (SEQ ID 23) |
| EISAL (SEQ ID 24) | E3: EISALEKEISALEKEISALEK-NH2 (SEQ ID 25) |
| EISAL (SEQ ID 24) | E4: EISALEKEISALEKEISALEKEISALEK-NH2 (SEQ ID 26) |
| KISAL (SEQ ID 27) | K3: KISALKEKISALKEKISALKE-NH2 (SEQ ID 28) |
| KISAL (SEQ ID 27) | K4: KISALKEKISALKEKISALKEKISALKE-NH2 (SEQ ID 29) |
| EVAAL (SEQ ID 30) | E3: EVAALEKEVAALEKEVAALEK-NH2 (SEQ ID 31) |
| EVAAL (SEQ ID 30) | E4: EVAALEKEVAALEKEVAALEKEVAALEK-NH2 (SEQ ID 32) |
| KVAAL (SEQ ID 33) | K3: KVAALKEKVAALKEKVAALKE-NH2 (SEQ ID 34) |
| KVAAL (SEQ ID 33) | K4: KVAALKEKVAALKEKVAALKEKVAALKE-NH2 (SEQ ID 35) |
| EVSAL (SEQ ID 14) | E3: EVSALEKEVSALEKEVSALEK-NH2 (SEQ ID 36) |
| EVSAL (SEQ ID 14) | E4: EVSALEKEVSALEKEVSALEKEVSALEK-NH2 (SEQ ID 37) |
| KVSAL (SEQ ID 16) | K3: KVSALKEKVSALKEKVSALKE-NH2 (SEQ ID 38) |
| KVSAL (SEQ ID 16) | K4: KVSALKEKVSALKEKVSALKEKVSALKE-NH2 (SEQ ID 39) |

For the purpose of the invention, the preferred type of a coiled coil is a dimer, either a heterodimer (heterocoil) of two different, but matching helices, which differ in at least one amino acid in the coil repeat sequence, or else a homodimer of two identical matching helices, i.e. those comprising the matching coil repeat sequences (the "coils").

The preferred number of coil repeats is 3-5, preferably any of the combinations 3+3, 3+4, 3+5, 4+4, 4+5, 5+5, 4+3, 5+3 or 5+4.

As an alternative to heptad repeats (repeats of an amino acid sequence consisting of 7 amino acids, 7-mers), 6-mers, 8-mers, or 9-mers may be used.

In case of a homodimeric coiled coil, the typical number of coil repeats is specifically not more than 5, so to avoid undesired mismatches of the structure. In case of a heterodimeric coiled coil, it is typically desirable to employ a length of the peptide sequence with at least 3 coils. Thereby the binding of the components of the vaccine, i.e. the directed adjuvant and the immunogen components, to each other is typically achieved with preferred high affinity of a Kd of less than $10^{-7}$ M, more preferred less than $10^{-8}$ M or $10^{-9}$ M. However, although more repeats increase the affinity, this may be at the cost of increased homodimerisation The components of the immunogenic composition of the invention may also comprise a peptide spacer so to link the anti-CD32 moiety and/or the TLR9 ligand, and optionally also the epitope (of the peptide immunogen) with the coil repeats, respectively. For example, the peptide spacer can be on either or both ends of a coiled coil. Each of the peptide spacers can be attached to a single alpha helix coiled coil domain of the coiled coil.

The peptide spacer can be, for example, a peptide of 5, 6, 7, 8, 9, 10, 15, 20, 25, 30, 35, 40, 45 or 50 amino acids or more, either linear or branched, e.g. to provide for two, three, four, or more branches. The number of amino acids in the peptide spacer may be, in some embodiments, 20 amino acids or up to 10 amino acids greater or fewer, depending on the particular sequences and length of the coil.

The term "anti-CD32 moiety" as used herein shall mean a ligand specifically binding to the cellular target CD32, either CD32a, CD32b or both, CD32a and CD32b. The moiety can be any binding structure, such as derived from proteins, polypeptides or peptides, including antibodies and antibody fragments or composite molecules with a binding part. The binding part of the molecules or molecule complex of the invention can be comprised of proteins such as antibodies or antibody fragments, such as Fab, Fv, scFv, dAb, F(ab)2, minibody, small mutated immunoglobulin domains, or other biological binders, such as soluble T-cell receptor, Darpins, etc. Antibodies and antibody fragments and derivatives may be generated and selected for binding to CD32 according to known methods such as hybridoma technology, B-cell cloning, phage display, ribosome display or cell surface display of antibody libraries, array screening of variant antibodies. Exemplary anti-CD32 moieties are scFv derived from the anti CD32 monoclonal antibody AT-10[25], IV.3[26], 2E1[27] or any other aCD32 monoclonal antibody.

The specific binding may be determined in a suitable binding assay, such as conventional immunoassays. There are numerous methods known in the art for detecting binding in an immunoassay. Various immunoassays known in the art can be used including competitive and non-competitive assay systems using techniques such as radioimmunoassays, ELISA (enzyme linked immunosorbent assay), immunoradiometric assays, gel diffusion precipitation reactions, immunodiffusion assays, western blot, BIAcore etc.

The term "cross-reactive" with respect to antigens or antibodies as used herein shall refer to epitopes shared between antigens of different origin, e.g. from human, rhesus monkey or mouse origin. The N-terminal epitope consisting or comprising the first 4 AA of G17 was found to be cross-reactive in peptides of various origin, which epitope triggers an immune response and IgG antibodies that are cross-reactive with the epitopes.

The immunogenic composition of the invention is specifically useful to treat gastrin dependent diseases or disease conditions that are associated with excess gastrin, e.g. gastrin dependent tumors or gastrin dependent cancer, such as pancreatic cancer, gastric ulcer, gastroesophageal reflux disease (GERD), end-stage renal failure (ESRF), or obesity.

The term "gastrin dependent tumor" or "gastrin dependent cancer" as used herein shall refer to tumors or disease or disease conditions associated therewith, of e.g. gastrin-dependent colorectal adenocarcinoma and other gastrin-dependent cancers such as stomach, liver, pancreatic and small cell carcinoma of the lungs. The term is specifically used herein with regard to treating the tumor for preventing tumor disease progression, for a positive tumor response or for tumor shrinkage. The term is also applied to minimal residual disease, which would be successfully treated, e.g. targeting circulating tumor cells to reduce their number below a certain threshold, e.g. below the detection limit.

Gastric ulcer disease, may be caused by increased stomach acid and a breakdown of the complex stomach defenses that normally protect the gastric mucosa from acid damage. Although the two conditions have different etiologies, both benefit from a reduction in gastric acid secretion. Gastric acid is produced in a specialized stomach cell, the parietal cell. Parietal cells can be stimulated to secrete acid by acetylcholine, histamine and gastrin, upon the binding of each of these compounds with specific receptors on the surface of the cell. Of these the most potent stimulator of acid secretion is the peptide hormone gastrin. The anti-gastrin immunotherapy therapy as described herein, would ameliorate the gastric ulcer disease conditions.

The term "gastrin-17 peptide" or "G17 peptide" or "G17" as used herein shall refer to the little gastrin G17, which consists of the N-terminal 17 AA of gastrin. The G17 peptide may be of human origin, or other mammalian origin, including rhesus monkey, or mouse, thus, has a human or other mammalian sequence, or may be an artificial construct, such as to incorporate artificial sequences, e.g. obtained by changing the type and/or sequence of amino acid residues in the native (naturally occurring) G17 sequence. The term shall specifically include variants of human G17, with an amino acid sequence of SEQ ID 1, or fragments thereof, but differs from its peptide sequence, in that it is derived from a homologous sequence of a different species. These are referred to as naturally occurring variants or analogs. The term "analogs" shall also refer to chimeric constructs originating from two or more origins, wherein at least one part is naturally occurring, e.g. which constitutes the major part (at least 50%) of the peptide immunogen, and another part is different thereto, either naturally occurring or synthetic (artificial).

The term shall specifically include fragments or functionally active variants of G17, e.g. those comprising one or more point mutations, or else peptides or polypeptides comprising further amino acid sequences besides the G17, e.g. by extending the N-terminus and/or the C-terminus by additional one or more amino acid residues or sequences. An extension of the C-terminus is e.g. preferred with repeats of G17 sequences, either identical or not, or with further amino acid sequences of gastrin.

The term shall specifically include the peptides with one or more modified amino acid residues. Common modifications include phosphorylation, methylation, acetylation, amidation, formation of pyrrolidone carboxylic acid, isomerization, hydroxylation, sulfation, flavin-binding, cysteine oxidation and nitrosylation. The exemplary modification as described herein is the modification of the N-terminal glutamic acid of G17, i.e. the pyroGlu at position 1, which is also known as "Pyrrolidone carboxylic acid (Glu)" or pGlu or pE.

The term "functionally active variants" as used herein with respect to the peptide immunogen of the invention, shall mean a sequence resulting from modification of this sequence (a parent sequence), e.g. by insertion, deletion or substitution of one or more amino acids, such as by recombination techniques or chemical derivatization of one or more amino acid residues in the amino acid sequence, or nucleotides within the coding nucleotide sequence, or at either or both of the distal ends of the sequence, and which modification does not affect (in particular impair) the activity of this sequence. In the case of a peptide immunogen eliciting a certain immune response to target gastrin, the functionally active variant of the peptide immunogen would still incorporate the antigenic determinant or epitope, though this could be changed, e.g. to increase the immunogenicity. Specifically, the functionally active variants of the G17 peptide immunogen, or a fragment thereof, such as the G12 or G13 fragment, have the potency to elicit IgG anti-gastrin antibodies in a treated subject, which antibodies cross-react with the endogenous gastrin of the subject.

Functionally active variants may be obtained, e.g. by changing the sequence of a parent peptide, e.g. the human, rhesus monkey or murine G17 peptide, or a fragment thereof, e.g. the G12 or G13 peptide, by introducing one or more modifications that do not substantially impair the cross-reactive epitopes, to obtain a molecule with substantially the same immunogenicity. The term "substantially the same immunogenicity" as used herein refers to the amount of an immune response or anti-gastrin IgG antibodies induced in a subject treated with the immunogenic composition, which amount is preferably at least 20% at least 30% at least 40%, at least 50% at least 60%, at least 70%, at least 80%, at least 90%, at least 95%, at least 98% or even at least 100% or at least 110%, or at least 120%, or at least 130%, or at least 140%, or at least 150%, or at least 160%, or at least 170%, or at least 180%, or at least 190%, e.g. up to 200% of the amount as determined for the parent peptide.

In a preferred embodiment the functionally active variant of a parent peptide a) is derived from the peptide by at least one amino acid substitution, insertion (addition) and/or deletion, e.g. comprising one or more point mutations wherein the functionally active variant has a specific sequence identity to the parent molecule, such as at least 50% sequence identity, preferably at least 60%, more preferably at least 70%, more preferably at least 80%, still more preferably at least 90%; and/or b) consists of the peptide and additionally at least one amino acid heterologous to the peptide.

Functionally active variants may be obtained by sequence alterations in the peptide sequence, e.g. by one or more point mutations, wherein the sequence alterations substantially retains a function of the unaltered peptide sequence, when used in according to the invention. Such sequence alterations or point mutations can include, but are not limited to, (conservative) substitutions, additions, deletions, mutations and insertions, e.g. the alteration of 1, 2, 3, or 4 amino acids, or by addition or insertion of one to several amino acids, e.g. 1, 2, 3, or 4 amino acids, or by a chemical derivatization of one to several amino acids, e.g. 1, 2, 3, or 4, or combination thereof, preferably by point mutations that are not contiguous. The substitutions in amino acid residues may be conservative substitutions, for example, substituting one hydrophobic amino acid for an alternative hydrophobic amino acid.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

Preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).
The "positively" charged amino acids are:
Arginine: (Arg, R) polar, positive; and
Lysine: (Lys, K) polar, positive.
The "negatively" charged amino acids are:
Aspartic acid: (Asp, D) polar, negative; and
Glutamic acid: (Glu, E) polar, negative.

"Percent (%) amino acid sequence identity" with respect to the peptide sequences described herein is defined as the percentage of amino acid residues in a candidate sequence that are identical with the amino acid residues in the specific peptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

Functionally active variants may be obtained by any of the known mutagenesis methods, including point mutations at desired positions, e.g. obtained by randomization techniques. In some cases positions are chosen randomly, e.g. with either any of the possible amino acids or a selection of preferred amino acids to randomize the peptide sequences. In this regard, the term "mutagenesis" refers to any art recognized technique for altering a polynucleotide or polypeptide sequence.

The term "immunogen" or "peptide immunogen" as used herein shall mean an antigen or immunogen of peptidic structure, in particular an immunogen that comprises or consists of a peptide of a specific amino acid sequence, which is either provided as a linear peptide or branched peptide, comprising naturally occurring amino acid residues or modified ones, e.g. a derivative obtained by modification or chemical derivatization, such as by phosphorylation, methylation, acetylation, amidation, formation of pyrrolidone carboxylic acid, isomerization, hydroxylation, sulfation, flavin-binding, cysteine oxidation and nitrosylation.

The peptide immunogen is specifically designed to trigger an immune response in a subject, and particularly includes one or more antigenic determinants, which can be possibly recognized by a binding site of an antibody or is able to bind to the peptide groove of HLA class I or class II molecules or other antigen presenting molecules such as CD1 and as such may serve as stimulant for specific T cells. The target antigen is either recognized as a whole target molecule or as a fragment of such molecule, especially substructures, e.g. a polypeptide or carbohydrate structure of targets, generally referred to as "epitopes", e.g. B-cell epitopes, T-cell epitope, which are immunologically relevant, i.e. are also recognizable by natural or monoclonal antibodies. Herein the use of B cell epitopes is preferred.

The term "epitope" as used herein according to the present invention shall in particular refer to a molecular structure which may completely make up a specific binding partner or be part of a specific binding partner to a binding site of an antibody. Chemically, an epitope of a peptide immunogen of the present invention may be a peptide epitope that usually includes at least 3 amino acid residues, preferably 4, 5, 6, 7, 8, 9, 10, 11, 12 or 13 amino acids. There is no critical upper limit to the length of the peptide, which could comprise even the full length of an amino acid sequence of a protein.

One or more epitopes of the same antigen or different antigens may be used according to the present invention.

The peptide immunogen of the invention is specifically understood as a self-antigen. The term "self-antigen" as used herein means any antigen, specifically polypeptide or peptide produced by a normal, healthy subject that does not elicit an immune response as such. These self-antigens may be produced at aberrant or high levels in certain disease states, including cancer disease, so called tumour associated antigens (TAAs). Herein, the human gastrin or human G17 is understood as a self-antigen in human subjects, and specifically as a TAA in subjects suffering from a gastrin dependent tumor.

It is understood that the self-antigens such as used according to the invention, can be naturally occurring, recombinantly or synthetically produced. It is also understood that the self-antigens need not be identical to the naturally produced antigen, but rather can include variations thereto having certain sequence identities, similarities or homology.

The peptide immunogen or the immunogenic composition used in the vaccine according to the invention, is usually contained in a vaccine in an effective amount, which is herein specifically understood as "immunologically effective amount". By "immunologically effective amount", it is meant that the administration of that amount to a subject, either in a single dose or as part of a series of doses, is effective on the basis of the therapeutic or prophylactic objectives. This amount will vary depending upon the health and physical condition of the subject to be treated, age, the capacity of the subject's immune system to synthesize antibodies, the degree of immune response desired, the formulation of the vaccine, and other conditions.

The invention also provides a method for treating a subject or raising an immune response in a subject, comprising the step of administering an immunologically effective amount of the peptide immunogen, the immunogenic composition or the vaccine of the invention.

An effective amount or dosage may range from 0.0001 to 2 mg, e.g. between 0.001 and 2 mg, of the immunogenic composition administered to the subject in need thereof, e.g. an adult human subject. The effective dosage of the immunogenic composition is capable of eliciting an immune response in a patient of effective levels of antibody titer to bind and neutralize endogenous mature and precursor G17 for, e.g. 1-3 months after immunization. The effectiveness of the therapy may be assayed by the anti-gastrin antibody titers in samples of blood taken from the subject.

The term "TLR9 ligand" as used herein is understood in the following way.

Toll-like receptor 9 (TLR9) recognizes unmethylated bacterial CpG DNA and initiates a signalling cascade leading to the production of proinflammatory cytokines. There are numerous structures or sequences that have been shown to act as a ligand of TLR9, i.e. bind to this receptor and thereby either activate (stimulate, upregulate, TLR9 agonist) or de-activate (downregulate, TLR) antagonist) TLR9. For instance, microbial DNA or synthetic DNA, e.g. synthetic CpG ODN may stimulate TLR9 with variations in the number and location of CpG dimers, as well as the precise base sequences flanking the CpG dimers. Synthetic CpG ODN differ from microbial DNA in that they have a partially or completely phosphorothioated backbone instead of the typical phosphodiester backbone and may or may not have a poly G tail at the 3' end, 5' end, or both.

The term "agonist" in conjunction with the TLR9 ligand as used herein shall specifically refer to the binding and activation of TLR9 in a cell-based assay.

The TLR9 ligand which is composed of a nucleotide sequence is typically coupled to the directed adjuvant component of the present immunogenic composition by chemical coupling e.g. using the commercially available KIT from Solulink. A peptidic TLR9 ligand may be coupled using standard peptide chemistry or may be integrated using recombinant DNA technology.

Exemplary TLR9 ligands are ODN 2216[28] (group 1), ODN 2006/ODN 2007[21] (group2) and CpG-M362[19] (group 3).

Further exemplary TLR9 ligands may be peptides that mimic the action of a CpG TLR9 agonist, e.g. identified by or obtained from a peptide library, which are selected for the affinity to bind the TLR9 and proven agonistic activity, or protein ligands, including specific antibodies.

The function of a TLR9 ligand or agonist may be determined in a suitable assay, e.g. in the following way: pDCs are purified from blood of a healthy donor as described by Tel et al[29] and subsequently incubated with the appropriate concentration of the TLR9 ligand. After 24 h IFNa is measured in the supernatant using standard ELISA protocols. For determination of the maturation state of the cells, pDCs are stained for expression of CD80 CD83 or CD86 using standard FACS procedures with commercially available specific antibodies before and after the incubation with the TLR9 ligand.

The number of reactive T cells that are activated upon exposure to the vaccine according to the invention may be determined by a number of methods including ELISPOT, FACS analysis, cytokine release, or T cell proliferation assays.

As used herein, the term "specificity" or "specific binding" refers to a binding reaction which is determinative of the cognate ligand of interest in a heterogeneous population of molecules. Thus, under designated conditions (e.g. immunoassay conditions), one or more antigens are specifically bound by the respective binding site(s) of a binder, which does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred a least 1000 fold. It is well-understood that the term shall also refer to cross-reactive or multispecific binders that specifically recognize one or more different antigens.

The term "treatment" as used herein shall always refer to treating subjects for prophylactic (i.e. to prevent infection and/or disease status) or therapeutic (i.e. to treat diseases regardless of their pathogenesis) purposes. Treatment of a subject will typically be therapeutic in cases of cancer disease conditions, including gastrin dependent tumors or gastrin dependent cancer. However, in case of patients suffering from a primary disease, which are at risk of disease progression or at risk of developing a secondary disease condition or side reaction, e.g. which is dependent on the endogenous gastrin production of gastrin effects, the treatment may be prophylactic.

Treatment may be effected with the immunogenic composition or the vaccine according to the invention as the sole prophylactic or therapeutic agent or else in combination with any suitable means, e.g. including chemotherapy, or the use of antacids.

In cancer therapy, additional therapeutic treatments include, for instance, surgical resection, radiation therapy, chemotherapy, hormone therapy, anti-tumor vaccines, antibody based therapies, whole body irradiation, bone marrow transplantation, peripheral blood stem cell transplantation, and the administration of chemotherapeutic agents.

The term "combination" as used in this regard, e.g. with respect to the combination of compounds or treatments specifically refers to the concomitant, simultaneous, parallel or consecutive treatment of a subject.

For treatment the immunogenic composition or the vaccine according to the invention may be administered at once, or may be divided into the individual components and/or a number of smaller doses to be administered at intervals of time. The vaccine is typically administered at a concentration of 0.1 to 500 µg/mL, e.g. either subcutaneously, intradermal, intramuscularly, intravenous, orally, through inhalation or intranasally, with or without an additional adjuvant such as ALUM. It is understood that the precise dosage and duration of treatment is a function of the disease being treated and may be determined empirically using known testing protocols or by extrapolation from in vivo or in vitro test data.

The the immunogenic composition or the vaccine of the present invention can be administered by any suitable means and respective formulations for including, but not limited to, for example, any of the parenteral (including subcutaneous, intramuscular, intravenous and intradermal) injection, or local injection into the affected site, such as joints or into or around the tumor. In a preferred embodiment the vaccine is provided in a formulation for intramuscular, subcutaneous or intradermal injection.

The invention also provides a delivery device, e.g. a syringe, pre-filled with the vaccine according to the invention.

Typically upon priming a subject by a first injection of a vaccine according to the invention, one or more booster injections may be performed over a period of time by the same or different administration routes. Where multiple injections are used, subsequent injections may be made, e.g. within 1 to 52 weeks of the previous injection, or even more.

The vaccine typically may contain diluents, such as water, saline, glycerol, ethanol, etc. Additionally, as auxiliary substances, such as wetting or emulsifying agents, pH buffering substances, and the like, may be present among excipients. Typically, the vaccine according to the invention is prepared as an injectable, either as liquid solutions or suspensions, or solid forms suitable for solution in, or suspension in, liquid vehicles prior to administration. The preparations also may be emulsified or encapsulated in liposomes.

Administration of the vaccine according to the invention may be suitably and additionally be combined with any of the TLR9 agonists and/or further adjuvant measures, e.g. as separate entities in the same formulation or as separate formulations, to enhance the immune response.

An enhanced Th1 immune response may include an increase in one or more of the cytokines associated with a Th1 immune response (such as IFNγ), and an increase in activated macrophages.

An enhanced Th1 immune response may include one or more of an increase in antigen specific IgG antibodies, especially IgG1 antibodies.

For example, the immunogenic composition or the vaccine of the invention, may be in association (e.g. chemically or recombinantly linked, bound by affinity binding or a mixture of separate components) with one or more adjuvants and/or pharmaceutically acceptable excipients. The vaccine according to the invention may include one or more pharmaceutically acceptable excipients or vehicles, such as water, saline, glycerol, ethanol, etc. Additionally, auxiliary substances, such as wetting or emulsifying agents, pH buffering substances, and the like, may be present in such vehicles. Adjuvants may specifically be used to enhance the effectiveness of the vaccine. Adjuvants may be added directly to the vaccine compositions or can be administered separately, either concurrently with or shortly after, administration of the vaccine.

Suitable adjuvants include cytokines and similar compounds which help orchestrate an immune response to the immunogen. As used herein, the term "cytokine" is used as a generic name for a diverse group of soluble proteins and peptides which act as humoral regulators at nano-to picomolar concentrations and which, either under normal or pathological conditions, modulate the functional activities of individual cells and tissues. These proteins also mediate interactions between cells directly and regulate processes taking place in the extracellular environment.

Examples of cytokines include IL-1, IL-4, TNFα, IFNα, INFγ, GM-CSF, G-CSF

CpG oligonucleotides can also be used as an adjuvant in conjunction with presentation of respective epitopes. Other adjuvants include alum, (in)complete Freund's adjuvant, *B. pertussis* or its toxin, IC31, etc.

The components of the immunogenic composition, i.e. the directed adjuvant component, e.g. the anti-CD32 moiety linked to the TLR9 ligand and the first peptidic alpha-helix, and the immunogen component, e.g. comprising the peptide immunogen linked to the second peptidic alpha-helix that matches the first one, as well as the immunogenic composition or the vaccine, or any of its binding moieties or ligands and the immunogen with our without the coil repeats may be obtained by various methods known in the art, e.g. by purification or isolation from cell culture, recombinant technology or by chemical synthesis.

According to a specific embodiment, the immunogenic composition and/or the directed adjuvant component and/or the immunogen component thereof, is produced as a recombinant polypeptide, such as by recombinant DNA technology. As used herein, the term "recombinant" refers to a molecule or construct that does not naturally occur in a host cell. In some embodiments, recombinant nucleic acid molecules contain two or more naturally-occurring sequences that are linked together in a way that does not occur naturally. A recombinant protein refers to a protein that is encoded and/or expressed by a recombinant nucleic acid. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention. Recombinant cells contain at least one recombinant polynucleotide or polypeptide. "Recombination", "recombining", and generating a "recombined" nucleic acid generally encompass the assembly of at least two nucleic acid fragments. In certain embodiments, recombinant proteins and recombinant nucleic acids remain functional, i.e., retain their activity or exhibit an enhanced activity in the host cell.

Thus, the invention further refers to the production of the immunogenic composition or the components thereof, and the recombinant means for such production, including a nucleic acid encoding the amino acid sequence, an expression cassette, a vector or plasmid comprising the nucleic acid encoding the amino acid sequence to be expressed, and a host cell comprising any such means. Suitable standard recombinant DNA techniques are known in the art and described inter alia in Sambrook et al., "Molecular Cloning: A Laboratory Manual" (1989), 2nd Edition (Cold Spring Harbor Laboratory press).

Herein the term "subject" is understood to comprise human or mammalian subjects, including livestock animals, companion animals, and laboratory animals, in particular human beings, which are either patients suffering from a specific disease condition or healthy subjects.

The invention further provides a kit of components for preparing the immunogenic composition of the invention, e.g. a pharmaceutical kit comprising one or more containers filled with the components. The kits can be used in the above-described methods. In a particular embodiment, the kit further comprises instructions for using the components of the immunogenic composition or the prepared immunogenic composition or vaccine of the invention.

According to a specific example, the vaccine according to the invention comprises a recombinant polypeptide of

```
SEQ ID 40:
EVQLQQSGPELKKPGETVKISCKASGYTFTNYGMNWVKQAPGKGLKW

MGWLNTYTGESIYPDDFKGRFAFSSETSASTAYLQINNLKNEDMATY

FCARGDYGYDDPLDYWGQGTSVTVSSGGGGSGGGGSGGGGSDIVMTQ

AAPSVPVTPGESVSISCRSSKSLLHTNGNTYLHWFLQRPGQSPQLLI

YRMSVLASGVPDRFSGSGSGTAFTLSISRVEAEDVGVFYCMQHLEYP

LTFGAGTKLELKGSISAWSHPQFEKGPEVSALEKEVSALEKEVSALE

KEVSALEKEVSALEK
```

N-terminal underlined: sequence of ScFV specifically binding to CD32a;
Italic: Linker; any alternative linker commonly used in scFv preparations may be used
Bold: StrepTag II for purification, any alternative tag may be used, e.g. flag tag or HIS tag or no tag, in which case purification may make use of the heptad repeat alpha helix C-terminal double underlined: heptad repeat alpha helix (pepE) to form the coiled coil with the counter heptad repeat alpha helix in the immunogen (pepK).

In this example (SEQ ID 40) 5 repeats are used; more repeats may cause auto-aggregation and less repeats may reduce the affinity, in this case 4 repeats were used. The preferred minimal functional number of repeats for the coils used is 3 and the preferred maximum functional number is 5[22-24] but more repeats are feasible depending on the type of alpha helix is used. Limiting would be the number of repeats that start to induce homodimerization. Thus, homodimerization is specifically excluded.

Similar polypeptides may comprise a leader sequence, the amino acid sequence of a specific anti-CD32 moiety, which is e.g. a recombinant scFv, a linker, a tag for purification purposes and the sequence of the peptidic alpha-helix pepE. This construct with or without the TLR9 ligand is also called "warhead", which may then be used to construct a vaccine by combination with an immunogen linked to the counter alpha helix pepK.

According to another specific example, the anti-CD32 moiety is an anti-CD32a peptide with the sequence of SEQ ID 41: ADGAWAWVWLTETAVGAAK[30] used as an alternative to the ScFv.

According to a further example, a stable coiled coil is established between the warhead scFv and the immunogen.

It has proven that PBMC could be effectively stimulated with such immunogen or vaccine.

In a further example it could be shown that the warhead mediated enhanced antigen presentation. T cells were effectively stimulated when the immunogen with the coil (the pepK coil) interacted with the warhead containing the counterpart coil (the pepE coil).

In further examples treatment of pancreatic cancer in a mouse model and in a rhesus monkey model is described, using a warhead employing either the anti-CD32 scFv or the anti-CD32a peptide linked by the coiled coil to the G12 peptide immunogen. The appetite reduction and appetite control is described in the rhesus monkey model.

Therefore, the present invention provides for a unique immunogenic composition and vaccine, and respective applications.

The foregoing description will be more fully understood with reference to the following examples. Such examples are, however, merely representative of methods of practicing one or more embodiments of the present invention and should not be read as limiting the scope of invention.

EXAMPLES

Example 1: Exemplary Binders

CD32 Binding Region, Herein Also Called Anti-CD32 Moiety or CD32 Binder:

CD32a binders: Antibody specifically binding to CD32a: mAb IV.3[31]

ScFV derived from mAb IV.3 (VH-linker-VL):

(SEQ ID 42)

EVQLQQSGPELKKPGETVKISCKASGYTFTNYGMNWVKQAPGKGLKWMGWLNTYTGE
SIYPDDFKGRFAFSSETSASTAYLQINNLKNEDMATYFCARGDYGYDDPLDYWGQGTSV

<u>TVSS</u>GGGGSGGGGSGGGGSDIVMTQAAPSVPVTPGESVSISCRSSKSLLHTNGNTYLH

WFLQRPQSPQLLIYRMSVLASGVPDRFSGSGSGTAFTLSISRVEAEDVGVFYCMQHLEY

PLTFGAGTKLELKGSI

Underlined: VH domain

Bold: HL domain

Normal type set. Flexible linker (maybe any linker)

Anti-CD32a Peptide:[30]

(SEQ ID 43): ADGAWAWVWLTETAVGAAK

Group CD32a + b binders:
Antibody specifically binding to CD32a and CD32b: mAb AT-10
(AbD Serotec)

ScFV derived from mAb AT-10 (VH-linker-VL):
(SEQ ID 44)

<u>EVKLEESGGGLVQPGGSMKLSCVASGFTFSYYWMNWVRQSPEKGLEWVAEIRLKSNNY</u>

<u>ATHYAESVKGRFTISRDDSKNNVYLQMNNLRAEDTGIYYCNRRDEYYAMDYWGQGTSV</u>

<u>SVSS</u>GGGGSGGGGSGGGGSDIVLTQSPGSLAVSLGQRATISCRASESVDNFGISFMNW

FQQKPGQPRLLIYGASNQGSGVPARFSGSGSGTDFSLNIHPVEEDDAAMYFCQQSKEV

PWTFGGGTKLEIKGSI

Underlined: VH domain

Bold: HL domain

Normal type set. Flexible linker (maybe any linker)

IgG1 Fc fragment (CH2-CH3 domain):
(SEQ ID 45)

(PKSCDKTHTCPPCP)<u>PELLGGPSVFLFPPKPKDTLMISRTPEVTCVVVDVSHEDPEVKFN</u>

<u>WYVDGVEVHNAKTKPREEQYNSTYRVVSVLTVLHQDWLNGKEYKCKVSNKALPAPIEKTI</u>

<u>SKAKGQP</u>REPQVYTLPPSRDELKNQVSLTCLVKGFYPSDIAVEWESNGQPENNYKTTP

PVLDSDGSFFLYSKLTVDKSRWQQGNVFSCSVMHEALHNHYTQKSLSLSPGK

Between ( ) is hinge region, may be omitted

Underlined: CH2 domain

Bold: CH3 domain

TLR9 Binding Region or Moiety, Herein Also Called
TLR9 Binder or TLR9 Ligand

CpG class A
Group CpG-A:
ODN2216: (SEQ ID 46):
GGGGGACGATCGTCGGGGGG

CpG class B
Group CpG-B:
Natural ligands:
ODN2006: (SEQ ID 47):
TCGTCGTTTTGTCGTTTTGTCGTT CpG class C
Group CpG-C
ODNM362: (SEQ ID 48):
TCGTCGTCGTTCGAACGACGTTGAT Exemplary CD32 Binding Products with Coils ScFV-coil 1 (IV.3):
(SEQ ID 49)

<u>EVQLQQSGPELKKPGETVKISCKASGYTFTNYGMNWVKQAPGKGLKWMGWLNTYTGE</u>

<u>SIYPDDFKGRFAFSSETSASTAYLQINNLKNEDMATYFCARGDYGYDDPLDYWGQGTSV</u>

<u>TVSS</u>GGGGSGGGGSGGGGSDIVMTQAAPSVPVTPGESVSISCRSSKSLLHTNGNTYLH

WFLQRPQSPQLLIYRMSVLASGVPDRFSGSGSGTAFTLSISRVEAEDVGVFYCMQHLEY

-continued

PLTFGAGTKLELKGSI<i>SAWSHPQFEKGPEVSALEKEVSALEKEVSALEKEVSA</i>

<i>LEK</i>

Underlined: VH domain

Bold: HL domain

Normal type set. Flexible linker (maybe any linker)

In italics: pepE coil plus C' StrepTag II sequence and "GP" linker may be any flexible linker (StrepTag II may be removed or replaced by HIS Tag or any other tag)

ScFV-coil 2 (AT10):

(SEQ ID 50)

<u>EVKLEESGGGLVQPGGSMKLSCVASGFTFSYYWMNWVRQSPEKGLEWVAEIRLKSNNY</u>

<u>ATHYAESVKGRFTISRDDSKNNVYLQMNNLRAEDTGIYYCNRRDEYYAMDYWGQGTSV</u>

<u>SVSS</u>GGGGSGGGSGGGGSDIVLTQSPGSLAVSLGQRATISCRASESVDNFGISFMNWF

QQKPGQPPRLLIYGASNQGSGVPARFSGSGSGTDFSLNIHPVEEDDAAMYFCQQSKEV

PWTFGGGTKLEIKGSI<i>SAWSHPFEKGPEVSALEKEV</i>

<i>SALEKEVSALEKEVSALEKEVSALEK</i>

Underlined: VH domain

Bold: HL domain

Normal type set. Flexible linker (maybe any linker)

In italics: pepE coil plus at C' StrepTag II sequence and "GP" linker may be any flexible linker (StrepTag II may be removed or replaced by HIS Tag or any other tag)

Peptide-coil:

(SEQ ID 51)

ADGAWAWVWLTETAVGAAK<i>GPEVSALEKEVSALEKEVSALEKEVSALEKEVSALEK</i>

In italics: pepE coil plus "GP" linker may be any flexible linker

IgG1 Fc fragment-coil:

(SEQ ID 52)

(PKSCDKTHTCPPCP)PELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQPENNYKTTP

PVLDDGSFFLYSKLTVDKSRWQQGNVFSCSVMHEALHNHYTQKSLSLSPGK<i>GPEVSAL</i>

<i>EKEVSALEKEVSALEKEVSALEKEVSALEK</i>

Between () is hinge region may be omitted

Underlined: CH2 domain

Bold CH3 domain
In italics: pepE coil plus "GP" linker may be any flexible linker Exemplary TLR9 Binding Products with SH Group for Chemical Cross-Linking to the CD32 Binder Group CpG-A:
ODN2216_SH: (SEQ ID 46):
GGGGGACGATCGTCGGGGGG-SH

In bold flexible linker with SH group for chemical cross-linking to ScFV-coil (Maybe any linker and chemically reactive group e.g NH2 suited for chemical crosslinking)

Group CpG-B:
Natural ligands:
ODN2006_SH: (SEQ ID 47):
TCGTCGTTTTGTCGTTTTGTCGTT-SH

In bold flexible linker with SH group for chemical cross-linking to ScFV-coil (Maybe any linker and chemically reactive group e.g NH2 suited for chemical crosslinking)

Group CpG-C
ODNM362_SH: (SEQ ID 48):
TCGTCGTCGTTCGAACGACGTTGAT-SH

In bold flexible linker with SH group for chemical crosslinking to ScFV-coil (maybe any linker and chemically reactive group e.g NH2 suited for chemical crosslinking)

Exemplary Warhead, i.e. a Structure Comprising a CD32 Binder and a TLR9 Binder

Any representative from the group of CD32 binders chemically linked by any method with any representative of the group of TLR9 binders, where preferably the TLR9 binders are coupled to available Lysines (K) in the CD32 binders e.g. Also mixtures of different TLR9 binders may be coupled e.g. CpG-B natural or peptidic binders.

```
ScFV-coil1 (IV.3)
                                                (SEQ ID 49)
EVQLQQSGPELKKPGETVKISCKASGYTFTNYGMNWVKQAPGKGLKWM

GWLNTYTGESIYPDDFKGRFAFSSETSASTAYLQINNLKNEDMATYFC

ARGDYGYDDPLDYWGQGTSVTVSSGGGGSGGGSGGGGSDIVMTQAAPS

VPVTPGESVSISCRSSKSLLHTNGNTYLHWFLQRPGQSPQLLIYRMSV

LASGVPDRFSGSGSGTAFTLSISRVEAEDVGVFYCMQHLEYPLTFGAG

TKLELKGSISAWSHQFEKGPEVSALE KEVSALE KEV

SALE KEVSALE KEVSALE K

Lysines in coil structure (Italic) are preferred
or

Peptide-coil:
                                                (SEQ ID 51)
ADGAWAWVWLTETAVGAAKGPEVSALE KEVSALE KEV

SALE KEVSALE KEVSALE K

Lysines in coil structure (Italic) are preferred
```

Example 2: Using the Technology Platform in Oncology

Warhead based on ScFV-coil1 (IV.3)+ODNM362, and immunogen G17 from rhesus and cynomolgus monkey (G17RM). In the following pE is understood as pyroGlu.

```
Sequence of human immunogen little gastrin
(G17H, 1st 13 AA, SEQ ID 9):
pEGPWLEEEE EAYG Sequence of rhesus and cynomolgus monkey immuno-
gen little gastrin
(G17RM, 1st 13 AA, SEQ ID 53:
pEGPWMEEEE AAYG Sequence of mouse immunogen little gastrin
(G17M, 1st 13 AA, SEQ ID 54):
pERPRMEEEE EAYG differences to G17RM in bold
```

Final Product Immunogen G17RM 1-Coil and G17H 1-Coil:

```
G17RM_1-coil, SEQ ID 55:
pEGPWMEEEEAAYGGGSGGKVSALKEKVSALKEKVSALKEKVSALK

EKVSALKE

G17H_1-coil,
SEQ ID 56
pEGPWLEEEEAAYGGGSGGKVSALKEKVSALKEKVSALKEKVSALK

EKVSALKE in bold: a linker (can be any linker)

In italics: the pepK coil for interaction with
warhead
```

Ready-to-Use (Final Product) TYG100 1RM and TYG100 1H

Warhead as described above (based ScFV-coil1 IV.3) is mixed with G17RM_1-coil or G17H_1-coil in a ratio which indicates 100% of warhead is complexed with G17RM_1-coil or G17H_1-coil, without G17 free immunogen being present (molar ratio of ~1:1) and formulated on Alum. Thereby TYG100_1RM and TYG100_1H are produced.

Example 3: TYG100 1RM for Treatment of Gastrin Dependent Cancer e.g. Pancreatic Cancer 6 Balb/c Mice were immunized 3 times on day 0, day 14 and day 35 with TYG100_1RM or G17_1RM (without warhead) containing rhesus monkey G17 (58.4 μg/shot in 0.5 ml). Two weeks after last immunization, serum was taken and analyzed for the presence of IgG antibodies against G17RM, G17H and G17M (=G17 from the mouse)

TABLE 1

| Mouse nr | IgG titre against warhead (ScFV-coil1) | IgG titre against G17RM | IgG titre against G17H | IgG titre against G17M |
|---|---|---|---|---|
| 1 | $2.5 * 10^{-7}$ | $2.1 * 10^{-6}$ | $1.2 * 10^{-6}$ | $3.5 * 10^{-3}$ |
| 2 | $2.1 * 10^{-7}$ | $4.7 * 10^{-5}$ | $1.4 * 10^{-4}$ | $5.6 * 10^{-3}$ |
| 3 | $1.2 * 10^{-7}$ | $8.9 * 10^{-7}$ | $2.1 * 10^{-6}$ | $1 * 10^{-2}$ |
| 4 | $1.1 * 10^{-6}$ | $1.6 * 10^{-5}$ | $1.7 * 10^{-5}$ | $1 * 10^{-2}$ |
| 5 | $2.0 * 10^{-7}$ | $9.7 * 10^{-6}$ | $9.8 * 10^{-6}$ | nd |
| 6 | $5.8 * 10^{-7}$ | $4.7 * 10^{-6}$ | $6.5 * 10^{-6}$ | $3.7 * 10^{-3}$ |
| average | $4.1 * 10^{-7}$ | $1.3 * 10^{-5}$ | $2.9 * 10^{-5}$ | $6.6 * 10^{-3}$ |

Table 1 shows that all mice responded with IgG against the 2 components of the vaccine (warhead and G17RM). Importantly all mice produced IgG that cross reacted with human G17 and to a lesser extend with mouse G17 (G17M). The latter is remarkable because the first 13 amino acids of mouse G17 (pERPRMEEEE EAYG, SEQ ID 9) are different in 3 AA from G17RM (differences indicated as bold and underlined) and G17M is an autoantigen for the mouse. The antibodies recognizing G17M are therefore autoantibodies, indicating that TYG100_1RM has been able to break the natural tolerance against the auto-antigen G17M. There was no response against G17 when the G17-peptide was immunized without the warhead.

The capacity of a vaccine to induce an autoimmune response is a prerequisite for an anti-cancer vaccine, where all tumour associated antigens (TAA) are auto-antigens which are over expressed, e.g. overexpressed on tumour cells. Hence a vaccine composed of the warhead of TYG100_1RM combined with human G17 as immunogen can be used as vaccine for the treatment of gastrin dependent tumours such as pancreatic cancer.

Example 4: Exemplary Products Including a Dimer of the Peptide Immungen

Final Product Immunogen G17RM 2-Coil and G17H 2-Coil:

A dimer of G17RM (1st 13 AA of little gastrin) was chemically synthesized using a special flexible linker connecting the 2 peptides to one pepK coil
G17RM 2-Coil:
(SEQ ID 57: Part of an immunogenic composition of the invention, comprising two rhesus monkey gastrin peptides of SEQ ID 53, a branched linker sequence and a peptide alpha-helix (TYG100_2RM). This part may be linked to the suitable directed adjuvant by a coiled-coil linkage)

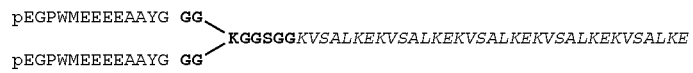

in bold a special flexible linker (can be any linker that connects three peptides)

In italics the pepK coil for interaction with warhead G17H 2-Coil:

(SEQ ID 11: Part of an immunogenic composition of the invention, comprising two human gastrin peptides of SEQ ID 9, a branched linker sequence and a peptide alpha-helix (TYG100_2H). This part may be linked to the suitable directed adjuvant by a coiled-coil linkage)

in bold a special flexible linker (can be any linker that connects three peptides)

In italics the pepK coil for interaction with warhead Final Product TYG100 2RM and TYG100 2H Warhead as described above (based on ScFV-coil1; IV.3) is mixed with G17RM_2-coil or G17H_2-coil in a ratio which indicates 100% of warhead is complexed with G17RM_2-coil or G17H_2-coil immunogen, without G17 free immunogen being present (molar ratio of ~1:1) and formulated on Alum. Thereby TYG100_2RM and TYG100_2H are produced.

Example 5: TYG100 2RM for Treatment of Gastrin Dependent Cancer e.g. Pancreatic Cancer 6 Balb/c Mice were immunized 3 times on day 0, day 14 and day 35 with TYG100_2RM containing the first 13 immuno acids of rhesus monkey G17 (66.8 µg/shot in 0.5 ml). Two weeks after last immunization, serum was taken and analyzed for the presence of IgG antibodies against G17RM, G17H and G17M (=G17 from the mouse)

TABLE 2

| Mouse nr | IgG titre against warhead (ScFV-coil1) | IgG titre against G17RM | IgG titre against G17H | IgG titre against G17M |
|---|---|---|---|---|
| 1 | $1 * 10^{-7}$ | $1.8 * 10^{-7}$ | $2.2 * 10^{-6}$ | $4.3 * 10^{-3}$ |
| 2 | $2.8 * 10^{-7}$ | $1.1 * 10^{-6}$ | $15.6 * 10^{-6}$ | $2.9 * 10^{-3}$ |
| 3 | $8.9 * 10^{-7}$ | $8.4 * 10^{-7}$ | $2.4 * 10^{-6}$ | $4.4 * 10^{-3}$ |
| 4 | $5.9 * 10^{-7}$ | $9.2 * 10^{-7}$ | $1.2 * 10^{-5}$ | $2.2 * 10^{-3}$ |
| 5 | $1.7 * 10^{-7}$ | $8.0 * 10^{-7}$ | $1 * 10^{-5}$ | $7.6 * 10^{-3}$ |
| 6 | $1.1 * 10^{-7}$ | $6.1 * 10^{-6}$ | $2.5 * 10^{-5}$ | $7.4 * 10^{-3}$ |
| average | $3.5 * 10^{-7}$ | $1.6 * 10^{-6}$ | $3.5 * 10^{-6}$ | $4.8 * 10^{-3}$ |

Table 2 shows that all mice responded with IgG against the 2 components of the vaccine (warhead and G17RM). Importantly all mice produced IgG that cross reacted with human G17 and to a lesser extend with mouse G17 (G17M). The latter is remarkable because the first 13 immuno acids of mouse G17 (pERPRMEEEE EAYG, SEQ ID 9) is different in 3 AA from G17RM (differences indicated as bold and underlined) and G17M is an auto antigen for the mouse. The antibodies recognizing G17M are therefore autoantibodies, indicating that TYG100_2RM has been able to break the natural tolerance against the auto-antigen G17M. There was no response against G17 when the G17 peptide was immunized without the warhead.

The capacity of a vaccine to induce an autoimmune response is a prerequisite for an anti-cancer vaccine, where all tumour associated antigens (TAA) are auto-antigens which are over expressed on tumour cells. Hence a vaccine composed of the warhead of TYG100_2RM combined with human G17 as immunogen can be used as vaccine for the treatment of gastrin dependent tumours such as pancreatic cancer. The responses against all 3 types of G17 induced by TYG100_2RM were stronger than those induced by TYG100_1RM (table 1), indicating that the dimer is preferred in the vaccine.

Example 6: TYG100 2RM for Treatment of Gastrin Dependent Cancer e.g. Pancreatic Cancer 6 Cynomolgus monkeys were immunized with TYG100_2RM and 6 were immunized with G17RM_2-coil on d0, d14 and d28. On d0, d14, d28, 42 and d56 serum was analyzed for the presence of IgG antibodies against autologous little gastrin (G17RM), little gastrin from humans (G17H), an irrelevant control peptide of similar MW as gastrin (control peptide) or against warhead (ScFV-coil1) using the multiplex ELISA system of Meso Scale Discovery (MSD) according to the MSD manual.

In FIG. 1, it can be seen that all 6 animals showed a strong time dependent IgG response to warhead (ScFV-coil1) as well as to G17RM and G17H, no response was seen against the control peptide. The response against G17RM after three immunizations was 75% of the response against ScFV-coil1. This is remarkable since G17RM is a 100% autologous protein of only ~1.2 kDa whereas ScFV-coil1 is a 100% allogeneic protein of >30 kDa. The anti G17RM antibodies cross reacted strongly with G17H. There was no response against G17RM when the G17RM_2-coil peptide was used without the warhead. The decrease in IgG titre between d42 and 56 was stronger for G17RM than it was for ScFV, indicating that part of the IgG antibodies were neutralized by endogenous G17. Importantly, the presence of endogenous G17 did not boost the response to G17RM.

The data in FIG. 1 show that the vaccine was able to induce a bonavide autoantibody response which is reversible. This is a prerequisite for anti-cancer vaccines, since tumour associated antigens (TAA) are auto-antigens which are over-expressed, e.g. overexpressed on tumour cells but also present at lower expression levels on normal healthy cells. Hence a vaccine such as TYG100_2RM or TYG100_2H can be used for the treatment of gastrin dependent tumours such as pancreatic cancer. Once the cancer has completely been cured, treatment may be stopped and the induced anti G17 antibodies will be cleared from the circulation. In order to maintain a steady state (during treatment) the autoimmune response needs to be boosted by repeated injections with the vaccine. No irreversible autoimmune disease is induced with this type vaccine.

Example 7: TYG100 2RM for Treatment of Obesity

The animals from Example 3 were monitored for their appetite and body weight was measured on d0, d14, d28, d42, and d56. After two injections with TYG100_2RM, 4 out of 6 animals lost interest in their daily snacks (biscuits), whereas basic food intake remained normal. This was accompanied by significant weight loss (FIG. 2), but no unwanted side effects were documented. So far such observations were never made with other vaccination with vaccines that were based on warhead and coiled coil interactions such as targeting immunogens other than gastrin immunogens (data not shown)

These data indicate that TYG100_2RM reduces craving for snacks (in between food) without influencing basic food intake needed for a healthy life. The animals were normally active and happy. Therefore, TYG100_2RM may be used for treatment of obesity.

REFERENCE LIST

1. Mathis, D. and C. Benoist. 2004. Back to central tolerance. *Immunity* 20:509-516.
2. Miller, J. F. A. P. and G. Morahan. 1992. Peripheral T cell tolerance. *Annu. Rev. Immunol.* 10:51-69.
3. Tafuri, A., J. Alferink, P. Möller, G. J. Hämmerling, and B. Arnold. 1995. T cell awareness of paternal alloantigens during pregnancy. *Science* 270:630-633.
4. Cheever, M. A. and C. S. Higano. 2011. PROVENGE (Sipuleucel-T) in prostate cancer: the first FDA-approved therapeutic cancer vaccine. *Clin. Cancer Res.* 17:3520-3526.
5. Linley, A. J., M. Ahmad, and R. C. Rees. 2011. Tumour-associated antigens: considerations for their use in tumour immunotherapy. *Int. J. Hematol.* 93:263-273.
6. Brett, B. T., S. C. Smith, C. V. Bouvier, D. Michaeli, D. Hochhauser, B. R. Davidson, T. R. Kurzawinski, A. F. Watkinson, S. N. Van, R. E. Pounder, and M. E. Caplin. 2002. Phase II study of anti-gastrin-17 antibodies, raised to G17DT, in advanced pancreatic cancer. *J Clin Oncol* 20:4225-4231.
7. Rengifo-Cam, W. and P. Singh. 2004. Role of progastrins and gastrins and their receptors in G I and pancreatic cancers: targets for treatment. *Curr. Pharm. Des* 10:2345-2358.
8. Watson, S. A., D. Michaeli, T. M. Morris, P. Clarke, A. Varro, N. Griffin, A. Smith, T. Justin, and J. D. Hardcastle. 1999. Antibodies raised by gastrimmune inhibit the spontaneous metastasis of a human colorectal tumour, AP5LV. *Eur J Cancer* 35:1286-1291.
9. Watson, S. A., T. M. Morris, D. F. McWilliams, J. Harris, S. Evans, A. Smith, and P. A. Clarke. 2002. Potential role of endocrine gastrin in the colonic adenoma carcinoma sequence. *Br. J Cancer* 87:567-573.
10. Morton, M., G. C. Prendergast, and T. D. Barrett. 2011. Targeting gastrin for the treatment of gastric acid related disorders and pancreatic cancer. *Trends in pharmacological sciences* 32:201-205.
11. Ciccotosto, G. D., J. K. Dawborn, K. J. Hardy, and A. Shulkes. 1996. Gastrin processing and secretion in patients with end-stage renal failure. *J Clin Endocrinol. Metab* 81:3231-3238.
12. Eaton-Bassiri, A., S. B. Dillon, M. Cunningham, M. A. Rycyzyn, J. Mills, R. T. Sarisky, and M. L. Mbow. 2004. Toll-like receptor 9 can be expressed at the cell surface of distinct populations of tonsils and human peripheral blood mononuclear cells. *Infect. Immun.* 72:7202-7211.
13. Saikh, K. U., T. L. Kissner, A. Sultana, G. Ruthel, and R. G. Ulrich. 2004. Human monocytes infected with *Yersinia pestis* express cell surface TLR9 and differentiate into dendritic cells. *J. Immunol.* 173:7426-7434.
14. Tanaka, J., K. Sugimoto, K. Shiraki, M. Tameda, S. Kusagawa, K. Nojiri, T. Beppu, K. Yoneda, N. Yamamoto, K. Uchida, T. Kojima, and Y. Takei. 2010. Functional cell surface expression of toll-like receptor 9 promotes cell proliferation and survival in human hepatocellular carcinomas. *Int. J Oncol.* 37:805-814.
15. Hartmann, G., J. Battiany, H. Poeck, M. Wagner, M. Kerkmann, N. Lubenow, S. Rothenfusser, and S. Endres. 2003. Rational design of new CpG oligonucleotides that combine B cell activation with high IFN-a induction in plasmacytoid dendritic cells. *Eur. J. Immunol.* 33:1633-1641.
16. Tversky, J. R., A. P. Bieneman, K. L. Chichester, R. G. Hamilton, and J. T. Schroeder. 2010. Subcutaneous allergen immunotherapy restores human dendritic cell innate immune function. *Clin. Exp. Allergy.* 40:94-102.
17. Abel, K., Y. Wang, L. Fritts, E. Sanchez, E. Chung, P. Fitzgerald-Bocarsly, A. M. Krieg, and C. J. Miller. 2005. Deoxycytidyl-deoxyguanosine oligonucleotide classes A, B, and C induce distinct cytokine gene expression patterns in rhesus monkey peripheral blood mononuclear cells and distinct alpha interferon responses in TLR9-expressing rhesus monkey plasmacytoid dendritic cells. *Clin Diagn. Lab Immunol* 12:606-621.
18. Puig, M., K. W. Tosh, L. M. Schramm, L. T. Grajkowska, K. D. Kirschman, C. Tami, J. Beren, R. L. Rabin, and D. Verthelyi. 2012. TLR9 and TLR7 agonists mediate distinct type I IFN responses in humans and nonhuman primates in vitro and in vivo. *J Leukoc. Biol.* 91:147-158.
19. Arndt, K. M., K. M. Muller, and A. Pluckthun. 2001. Helix-stabilized Fv (hsFv) antibody fragments: substituting the constant domains of a Fab fragment for a heterodimeric coiled-coil domain. *J Mol. Biol.* 312:221-228.
20. Van Reijsen, F. C., C. A. F. M. Bruijnzeel-Koomen, F. S. Kalthoff, E. Maggi, S. Romagnani, J. K. T. Westland, and G. C. Mudde. 1992. Skin-derived aeroallergen-specific T-cell clones of Th2 phenotype in patients with atopic dermatitis. *J. Allergy Clin. Immunol.* 90:184-193.
21. Krieg, A. M., A. K. Yi, S. Matson, T. J. Waldschmidt, G. A. Bishop, R. Teasdale, G. A. Koretzky, and D. M. Klinman. 1995. CpG motifs in bacterial DNA trigger direct B-cell activation. *Nature.* 374:546-549.
22. Chao, H., D. L. Bautista, J. Litowski, R. T. Irvin, and R. S. Hodges. 1998. Use of a heterodimeric coiled-coil system for biosensor application and affinity purification. *J. Chromatogr. B Biomed. Sci. Appl.* 715:307-329.
23. Litowski, J. R. and R. S. Hodges. 2001. Designing heterodimeric two-stranded alpha-helical coiled-coils: the effect of chain length on protein folding, stability and specificity. *J. Pept. Res.* 58:477-492.
24. Litowski, J. R. and R. S. Hodges. 2002. Designing heterodimeric two-stranded alpha-helical coiled-coils. Effects of hydrophobicity and alpha-helical propensity on protein folding, stability, and specificity. *J. Biol. Chem.* 277:37272-37279.
25. Greenman, J., A. L. Tutt, A. J. George, K. A. Pulford, G. T. Stevenson, and M. J. Glennie. 1991. Characterization of a new monoclonal anti-Fc gamma RII antibody, AT10, and its incorporation into a bispecific F(ab')2 derivative for recruitment of cytotoxic effectors. *Mol. Immunol* 28:1243-1254.
26. Stuart, S. G., M. L. Trounstine, D. J. Vaux, T. Koch, C. L. Martens, I. Mellman, and K. W. Moore. 1987. Isolation and expression of cDNA clones encoding a human receptor for IgG (Fc gamma RII). *J. Exp. Med.* 166:1668-1684.
27. Macintyre, E. A., P. J. Roberts, R. bdul-Gaffar, K. O'Flynn, G. R. Pilkington, F. Farace, J. Morgan, and D. C. Linch. 1988. Mechanism of human monocyte activation via the 40-kDa Fc receptor for IgG. *J Immunol.* 141:4333-4343.
28. Krug, A., S. Rothenfusser, V. Hornung, B. Jahrsdorfer, S. Blackwell, Z. K. Ballas, S. Endres, A. M. Krieg, and G. Hartmann. 2001. Identification of CpG oligonucleotide sequences with high induction of IFN-alpha/beta in plasmacytoid dendritic cells. *Eur J Immunol.* 31:2154-2163.
29. Tel, J., N. Beenhakker, G. Koopman, B. Hart, G. C. Mudde, and V. de, I. 2012. Targeted delivery of CpG ODN to CD32 on human and monkey plasmacytoid dendritic cells augments IFNalpha secretion. *Immunobiology.* 217: 1017-1024.
30. Berntzen, G., J. T. Andersen, K. Ustgard, T. E. Michaelsen, S. A. Mousavi, J. D. Qian, P. E. Kristiansen, V. Lauvrak, and I. Sandlie. 2009. Identification of a high affinity Fcgamma RIIA binding peptide that distinguishes Fcgamma RIIA from Fcgamma RIIB and exploits Fcgamma RIIA mediated phagocytosis and degradation. *J. Biol. Chem.* 284:1126-1135.
31. Stuart, S. G., N. E. Simister, S. B. Clarkson, B. M. Kacinski, M. Shapiro, and I. Mellman. 1989. Human IgG Fc receptor (hFcRII; CD32) exists as multiple isoforms in macrophages, lymphocytes and IgG-transporting placental epithelium. *EMBO J.* 8:3657-3666.

The invention claimed is:

1. An immunogenic composition comprising:
   (a) a directed adjuvant comprising at least an anti-CD32 moiety linked to a TLR9 ligand and a first peptidic alpha-helix, wherein:
      (i) the anti-CD32 moiety is a protein, polypeptide, or peptide specifically binding CD32 selected from the group consisting of specific CD32 binders, which are antibodies, antibody fragments, proteins, or peptides; and (ii) the TLR9 ligand is a TLR9 agonist selected from the group consisting of CpG oligodeoxynucleotide class A, B, and C; and (b) a gastrin-17 peptide immunogen linked to a second peptidic alpha-helix coiled to the first alpha-helix, wherein the peptide immunogen is a gastrin-17 peptide comprising the amino acid sequence of SEQ ID NOS:1, 6, 8, or 9; or of the peptide immunogen of SEQ ID NO:10, wherein said first and second peptidic alpha-helices are repeats of matching coil repeat sequences, which coil repeat sequences are selected from the group consisting of SEQ ID NOs: 14, 16, 18, 21, 24, 27, 30, and 33.

2. The immunogenic composition according to claim 1, wherein said peptide immunogen is a linear peptide comprising or consisting of the amino acid sequence of SEQ ID NO:9.

3. The immunogenic composition according to claim 1, which comprises at least two of the peptide immunogens linked to the second peptidic alpha-helix.

4. The immunogenic composition according to claim 1, wherein each of said first and second alpha-helices comprises 3-5 amino acid repeats of an amino acid motif, specifically binding to each other with a Kd of less than $10^{-6}$ M.

5. The immunogenic composition according to claim 1, which comprises one or more linker sequences comprising glycine and/or serine and/or lysine residues.

6. The immunogenic composition according to claim 1, comprising the amino acid sequence of SEQ ID NO: 10 or SEQ ID NO: 11.

7. A kit for preparing the immunogenic composition according to claim 1, comprising the following components:
  (a) a directed adjuvant comprising at least an anti-CD32 moiety linked to a TLR9 ligand and a first peptidic alpha-helix, wherein:
    (i) the anti-CD32 moiety is a protein, polypeptide, or peptide specifically binding to CD32, selected from the group consisting of specific CD32 binders, which are antibodies, antibody fragments, proteins, or peptides; and
    (ii) the TLR9 ligand is a TLR9 agonist selected from the group consisting of a CpG oligodeoxynucleotide class A, B, and C; and
  (b) a gastrin-17 peptide immunogen linked to a second peptidic alpha-helix matching the first alpha-helix, wherein the peptide immunogen is a gastrin-17 peptide comprising the amino acid sequence of SEQ ID NOS:1, 6, 8, or 9; or of the peptide immunogen of SEQ ID NO:10, wherein said first and second peptidic alpha-helices are repeats of matching coil repeat sequences, which coil repeat sequences are selected from the group consisting of SEQ ID NOs: 14, 16, 18, 21, 24, 27, 30, and 33.

8. A method of treating a subject suffering from a gastrin dependent disease, the method comprising administering the immunogenic composition of claim 1.

9. The method of claim 8, wherein the composition is administered to the subject in an effective amount employing a prime-boost strategy.

10. The method of claim 8, wherein the composition is administered to the subject in an effective amount ranging from 0.0001 to 2 mg per administration.

11. The method of claim 8, wherein the subject is further treated by chemotherapy.

12. The method of claim 8, wherein a protective immune response in the subject is triggered to provide a serum IgG titer against human gastrin-17 of at least 1/1000.

13. The immunogenic composition according to claim 1, wherein said peptide immunogen is a linear peptide comprising or consisting of:
  (i) the amino acid sequence of SEQ ID NO:6; or
  (ii) the amino acid sequence of SEQ ID NO:8.

14. The immunogenic composition according to claim 1, which comprises two, three or four of the peptide immunogens linked to the second peptidic alpha-helix.

15. The immunogenic composition according to claim 1, wherein said anti-CD32 moiety targets CD32a.

16. The immunogenic composition according to claim 5, wherein at least one of the linker sequences is selected from the group consisting of SEQ ID NO:12 and SEQ ID NO:13.

17. The method of claim 8, wherein the gastrin dependent disease is a disease selected from the group consisting of pancreatic cancer, gastric ulcer, gastroesophageal reflux disease (GERD), end-stage renal failure (ESRF), and obesity.

18. The immunogenic composition according to claim 1, wherein the gastrin-17 peptide comprises the amino acid sequence of SEQ ID NOS:1, 6, 8, or 9.

19. The immunogenic composition according to claim 1, wherein the gastrin-17 peptide comprises the amino acid sequence of SEQ ID NOS:1, 2, or 9.

* * * * *